US011596430B2

(12) United States Patent
Mirza et al.

(10) Patent No.: US 11,596,430 B2
(45) Date of Patent: Mar. 7, 2023

(54) ENDOSCOPIC SURGICAL INSTRUMENT HAVING A RETRACTABLE CUTTING BLADE AND SURGICAL PROCEDURE USING SAME

(71) Applicant: A.M. SURGICAL, INC., Smithtown, NY (US)

(72) Inventors: Ather Mirza, Saint James, NY (US); Romi Mirza, Henderson, NV (US)

(73) Assignee: A.M. SURGICAL, INC., Smithtown, NY (US)

( * ) Notice: Subject to any disclaimer, the term of this patent is extended or adjusted under 35 U.S.C. 154(b) by 84 days.

(21) Appl. No.: 17/343,986

(22) Filed: Jun. 10, 2021

(65) Prior Publication Data

US 2021/0386448 A1 Dec. 16, 2021

Related U.S. Application Data

(60) Provisional application No. 63/037,872, filed on Jun. 11, 2020.

(51) Int. Cl.
*A61B 17/32* (2006.01)
*A61B 17/00* (2006.01)

(52) U.S. Cl.
CPC ........... *A61B 17/32002* (2013.01); *A61B 2017/00862* (2013.01); *A61B 2017/320032* (2013.01)

(58) Field of Classification Search
CPC ...... A61B 17/32002; A61B 17/320016; A61B 17/320036; A61B 17/3205; A61B 2017/00862; A61B 2017/320032; A61B 2017/320064; A61B 2017/00353; A61B 2017/320008; A61B 1/00128; A61B 1/3132; A61B 1/00087; A61B 1/00135; A61B 1/018
See application file for complete search history.

(56) References Cited

U.S. PATENT DOCUMENTS

| | | | |
|---|---|---|---|
| 5,306,284 A * | 4/1994 | Agee | A61B 17/320036 606/170 |
| 5,366,465 A | 11/1994 | Mirza | 606/170 |
| 7,041,115 B2 | 5/2006 | Mirza et al. | 606/170 |
| 7,780,690 B2 * | 8/2010 | Rehnke | A61B 17/320036 606/167 |
| 8,821,383 B2 | 9/2014 | Mirza et al. | 600/114 |
| 8,911,470 B2 | 12/2014 | Mirza et al. | 606/204 |

(Continued)

*Primary Examiner* — Erich G Herbermann
(74) *Attorney, Agent, or Firm* — Bodner & O'Rourke, LLP; Gerald T. Bodner; Christian P. Bodner

(57) ABSTRACT

An endoscopic surgical instrument includes a main body assembly, and a cannula having a lumen and formed with a slot. An inner tube, which houses a spring-biased retractable cutting blade assembly having a cutting blade, is mounted on one end of the main body assembly and extends axially therefrom. The tube is receivable within the lumen of the cannula, and may be particularly oriented within the cannula lumen such that the cutting blade may be caused to project from both the tube and the cannula slot. The inner tube has a bore in which the distal end of an endoscope may be received. The instrument may be locked in one position to allow the endoscope to engage the blade assembly and cause the cutting blade to project from the cannula slot during a tissue cutting procedure, or may be locked in another position wherein the cutting blade remains retracted.

46 Claims, 27 Drawing Sheets

(56) References Cited

U.S. PATENT DOCUMENTS

| | | |
|---|---|---|
| 8,979,880 B2 | 3/2015 | Mirza et al. .................. 606/170 |
| 8,992,424 B2 * | 3/2015 | Orbay ................ A61B 1/00052 |
| | | 600/183 |
| 9,066,746 B2 | 6/2015 | Mirza et al. |
| 9,179,930 B2 | 11/2015 | Mirza et al. |
| 9,211,136 B1 | 12/2015 | Mirza et al. |
| 9,408,623 B2 | 8/2016 | Mirza et al. |
| 9,445,830 B2 | 9/2016 | Mirza et al. |
| 9,610,089 B2 | 4/2017 | Mirza et al. |
| 9,808,274 B2 | 11/2017 | Mirza et al. |
| 9,931,133 B2 | 4/2018 | Mirza et al. |
| 10,201,372 B2 | 2/2019 | Mirza et al. |
| 10,265,093 B2 | 4/2019 | Mirza et al. |
| 10,548,624 B2 | 2/2020 | Mirza et al. |
| 11,051,848 B2 | 7/2021 | Mirza et al. |
| 11,096,720 B2 | 8/2021 | Mirza et al. |

* cited by examiner

SECTION A-A
SCALE 1.5 : 1

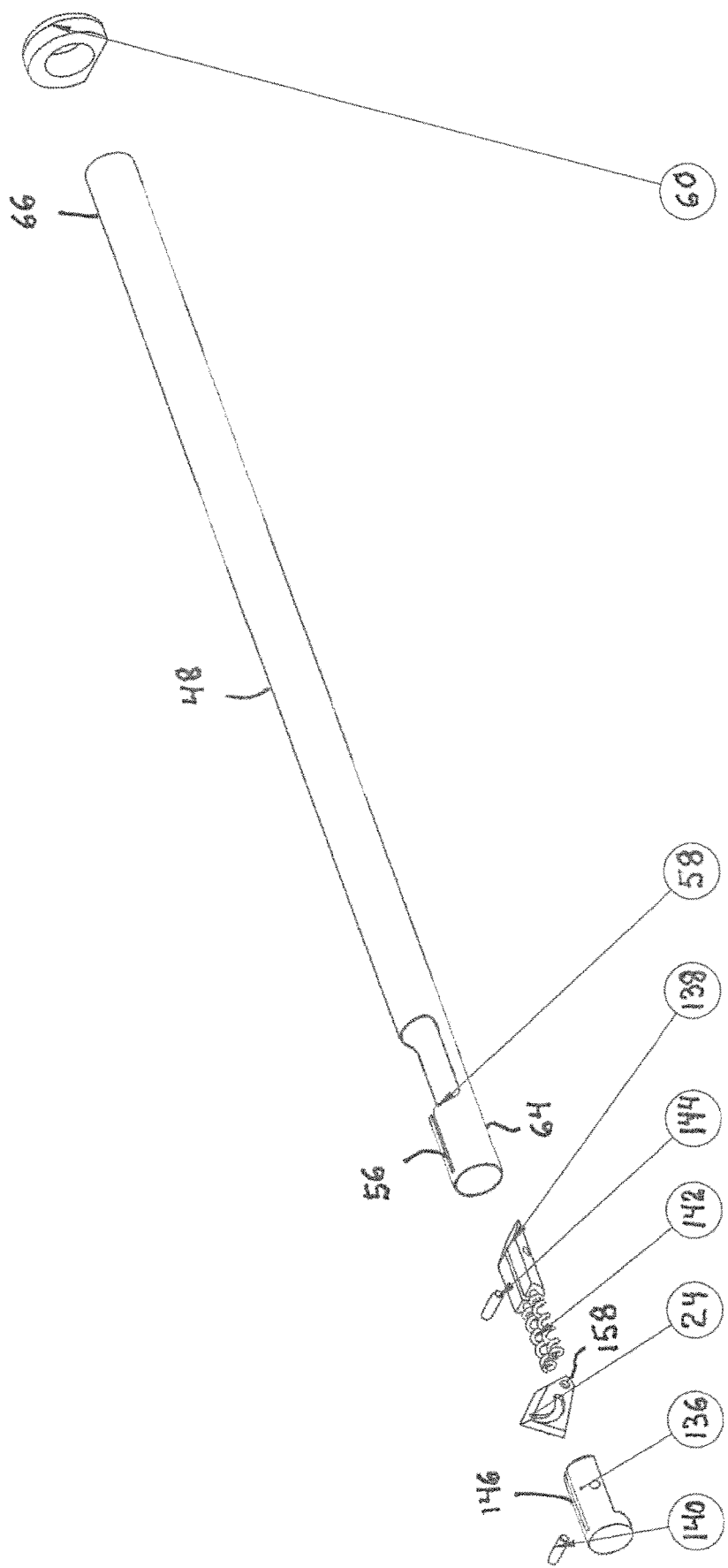

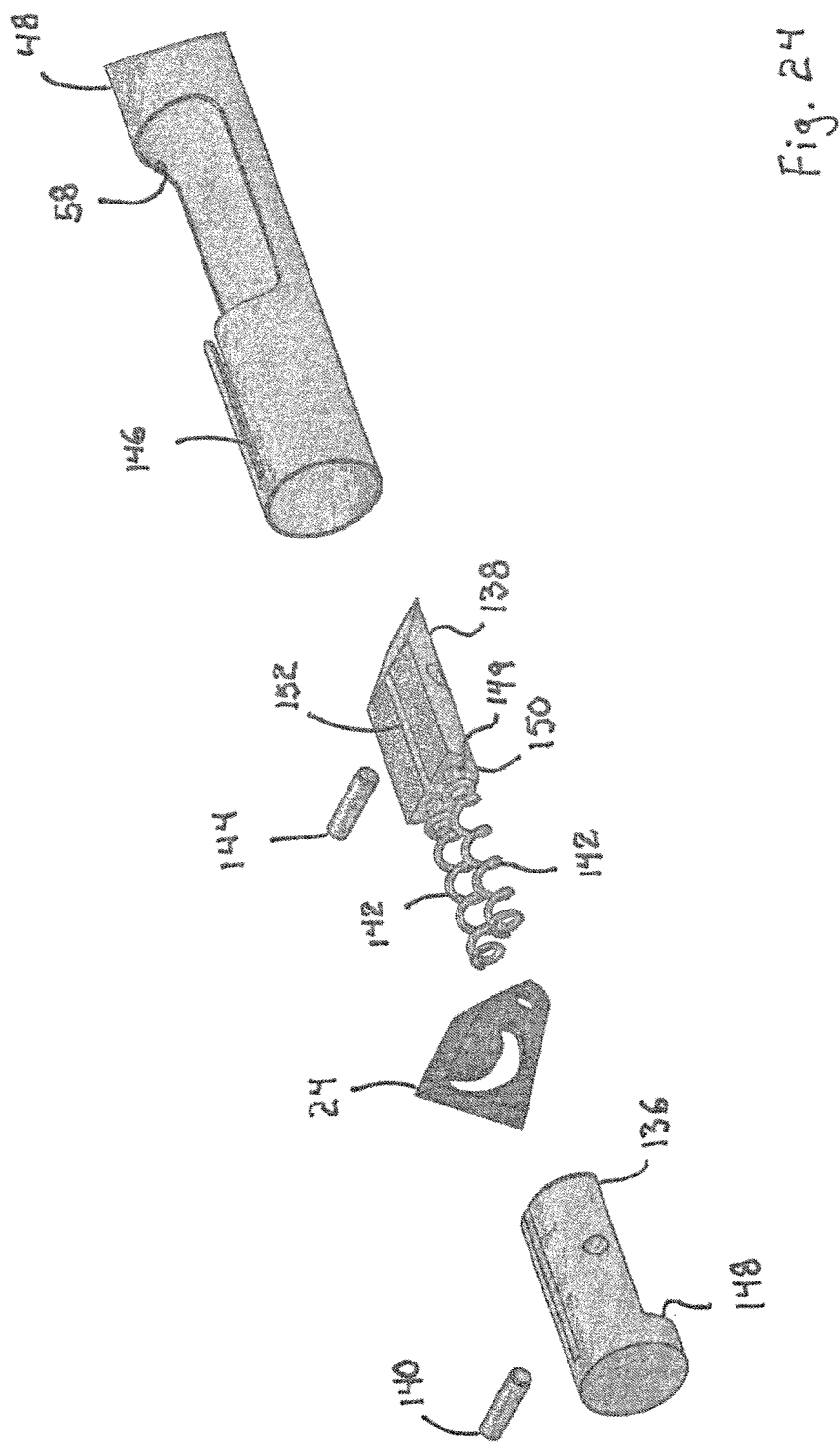

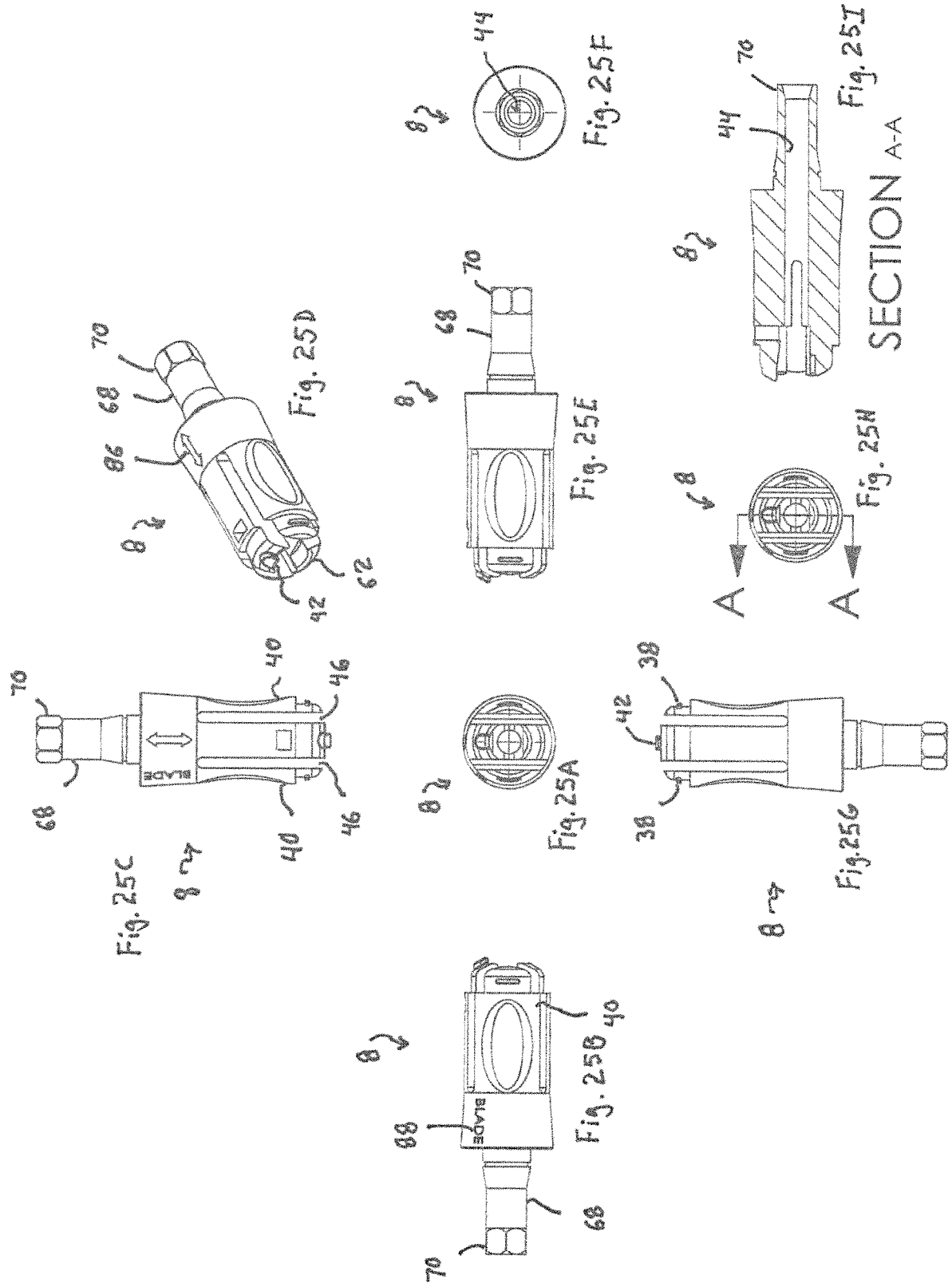

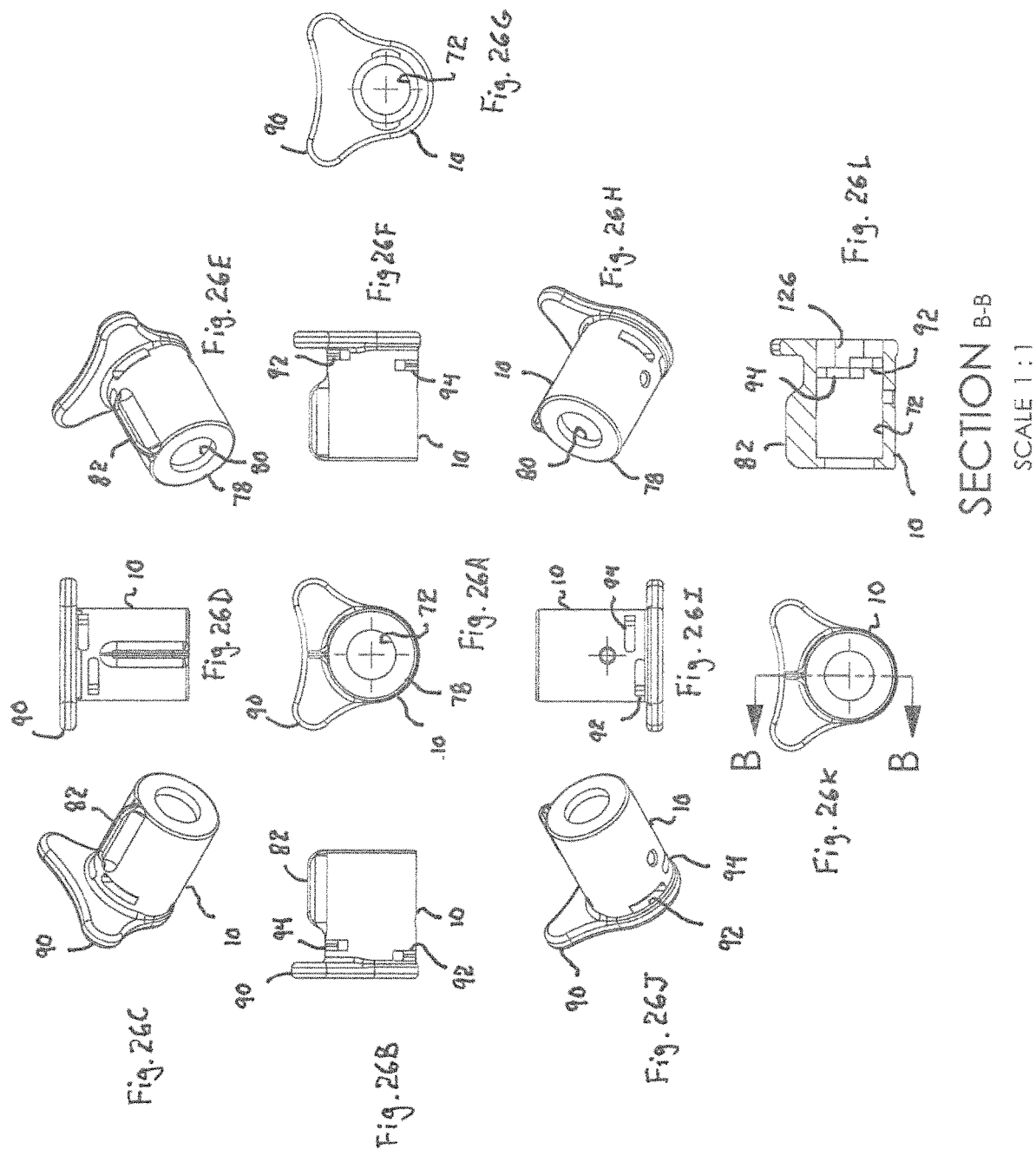

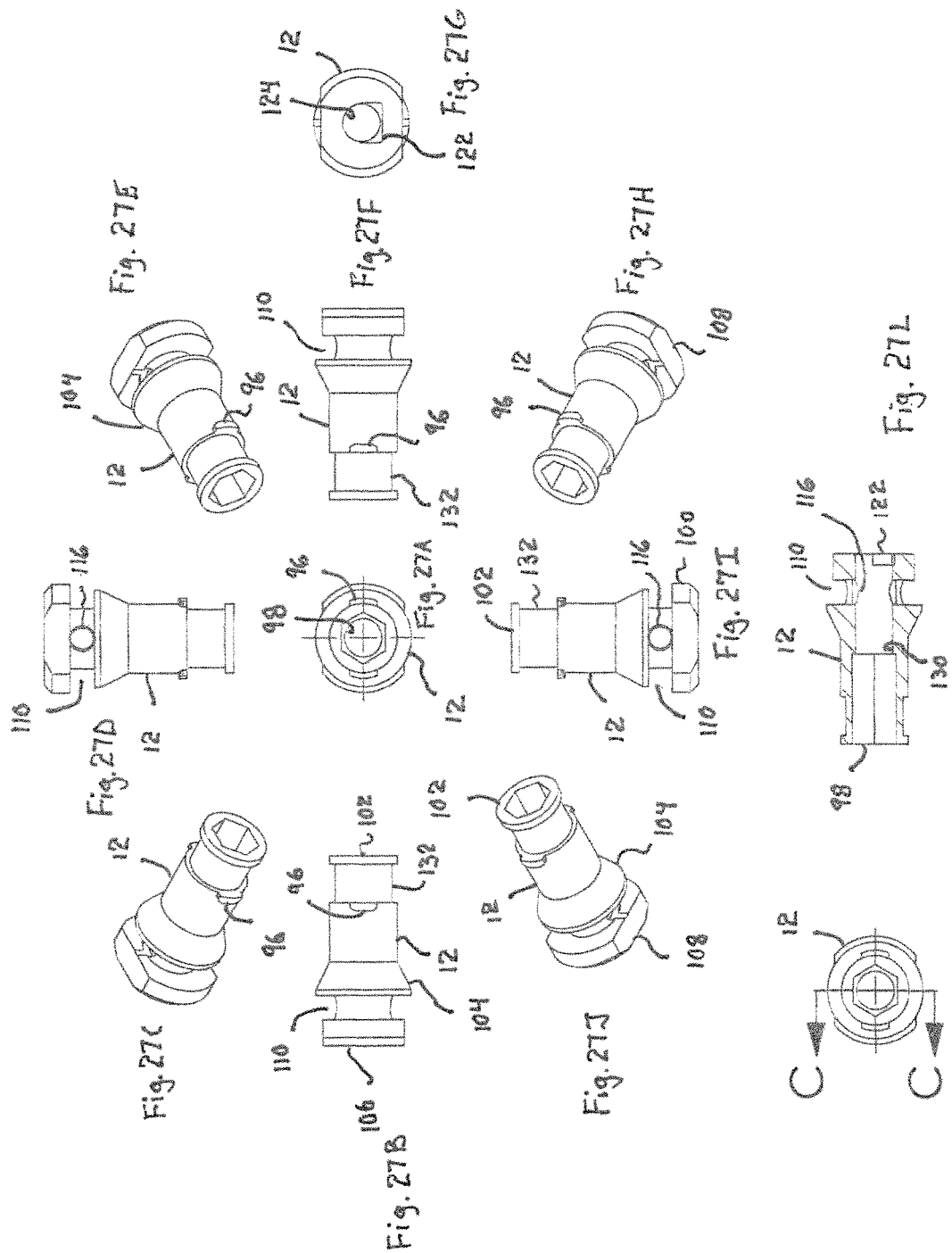

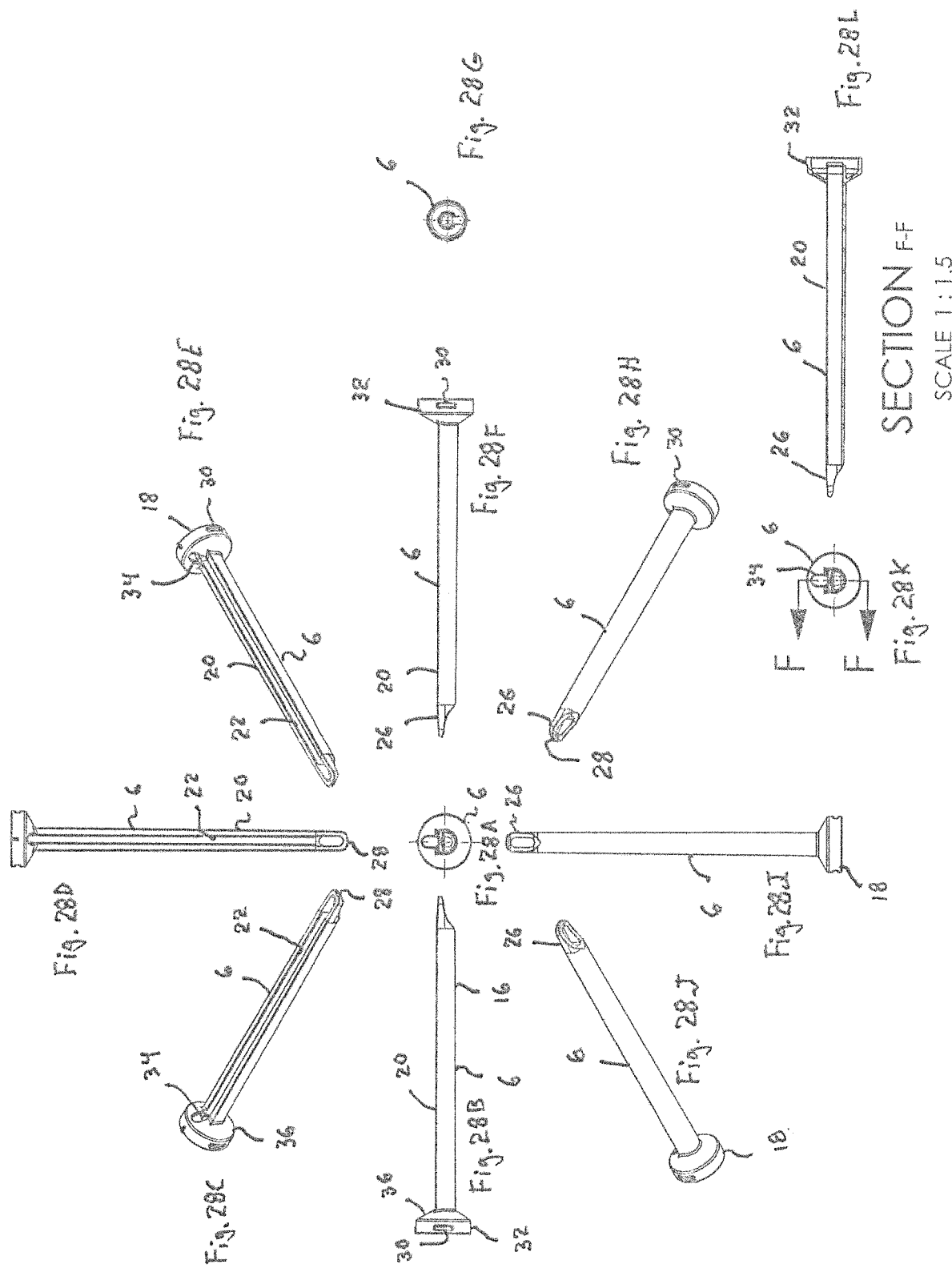

ENDOSCOPIC SURGICAL INSTRUMENT HAVING A RETRACTABLE CUTTING BLADE AND SURGICAL PROCEDURE USING SAME

CROSS-REFERENCE TO RELATED APPLICATIONS

This application is related to U.S. Provisional Patent Application Ser. No. 63/037,872, filed on Jun. 11, 2020, and titled "Endoscopic Surgical Instrument Having a Retractable Cutting Blade and Surgical Procedure Using Same", the disclosure of which is hereby incorporated by reference and on which priority is hereby claimed.

BACKGROUND OF THE INVENTION

Field of the Invention

The present invention generally relates to medical devices, and more particularly relates to devices and methods for endoscopic surgery. Even more specifically, this invention relates to procedures and endoscopic surgical instruments used in carpal tunnel or pulley release surgery, or any soft tissue release surgery (e.g., cubital tunnel and gastroc releases).

Description of the Prior Art

Endoscopic surgery is a minimally invasive surgical procedure that is performed through small incisions or natural body openings. An endoscopic procedure typically involves use of specialized devices and remote-control manipulation of instruments with indirect observation of the surgical field through an endoscope or similar device. Comparing to open surgery, endoscopic surgery may result in shorter hospital stays, or allow outpatient treatment.

Carpal tunnel syndrome is an entrapment median neuropathy resulting from compression of the median nerve at the wrist in the carpal tunnel. Symptoms of carpal tunnel syndrome include tingling, numbness, weakness, or pain felt in the fingers supplied by the median nerve or in the palm. Repetitive tasks, force, posture, and vibration have been cited as causative or contributing factors to carpal tunnel syndrome. Palliative treatments for carpal tunnel syndrome include direct corticosteroid injections, splinting, oral corticosteroids and/or behavior modification.

Typically, endoscopic surgery has involved a number of steps and separate devices for performing tendon, pulley or tunnel division. After making an incision and opening a path to the pulley or tunnel using a blunt instrument, a cannula is inserted into the path. Briefly, in order to smoothly insert the cannula, the central lumen of the cannula must be filled with a device, such as an obturator. The obturator is then removed and an endoscope, or arthroscope, is inserted into the cannula to view the pulley or tunnel. The endoscope is then withdrawn from the cannula, a knife is either advanced into the cannula for division or a specialized knife assembly is affixed to the endoscope and the knife/endoscope assembly is advanced into the cannula for division.

A.M. Surgical, Inc., the applicant herein, has developed and patented numerous compact surgical instruments for uniportal endoscopic pulley or tunnel release surgery that eliminate the need for a separate device, such as an obturator, for filling the cannula during insertion and eliminate the need to remove the endoscope in order to insert a cutting blade or blade assembly. Such instruments have revolutionized and simplified carpal tunnel surgical procedures, in particular, and many other surgical procedures, in general (for example, uniportal plantar fascia release, lateral release for patella realignment, release of the posterior and other compartments of the leg, and forearm fascia release for fascial compartment syndrome, and other endoscopic surgical divisions or partial separation of a tendon or ligament, cutting, dividing, separating or making an incision in connective tissue, muscle, cartilage, membranes, skin, other body tissues or organs, and other procedures).

One such endoscopic surgical instrument is disclosed in U.S. Pat. No. 8,911,470 (Mirza et al.), assigned of record to A.M. Surgical, Inc., the disclosure of which is incorporated herein by reference. The instrument includes a slotted clear (transparent) cannula, a cutting blade and a housing to which the slotted cannula is attached. The blade is "parked" within the instrument housing in a revolver assembly until deployed. The revolver assembly may be rotated to position the cutting blade in alignment with the cannula and, by doing so, the blade mounts to the distal end of a guidance tube passing through the housing and the revolver assembly. The guidance tube, with the cutting blade affixed to the end thereof, is advanced on the housing through the lumen of the cannula. The cutting blade protrudes through the cannula slot as it advances thereon from the proximate end to the distal end thereof such that any tissue or ligaments exposed to the cutting blade during a surgical procedure will be cut or severed. Other patents disclosing compact endoscopic surgical instruments that are assigned of record to A.M. Surgical include U.S. Pat. Nos. 8,979,880; 9,066,746; 9,179,930; 9,211,136; 9,408,623; 9,445,830; 9,610,089; 9,808,274; 9,931,133; 10,265,093; and 10,548,624, the disclosure of each of which is incorporated herein by reference.

The surgical instruments disclosed in the aforementioned patents work fine for their intended purpose, but each of these instruments has its cutting blade always protruding through the cannula slot when moved into the cannula. Thus, during a surgical procedure, when the cannula is properly positioned at the surgical site, any tissue or ligament in proximity to the cannula will be exposed to the cutting blade and will be cut or severed as the blade is advanced or retracted on the cannula.

OBJECTS AND SUMMARY OF THE INVENTION

It is an object of the present invention to provide an endoscopic surgical instrument having a retractable cutting blade.

It is another object of the present invention to provide an endoscopic surgical instrument having a retractable cutting blade sharpened at both edges which can perform a forward and retrograde (reverse) cut at the choice of the user.

It is a further object of the present invention to provide an endoscopic surgical instrument having a cannula formed with an axially-extending slot from which a cutting blade may be selectively caused to protrude or be retracted into the cannula at a selected position along at least a portion of the cannula.

It is still another object of the present invention to provide an endoscopic surgical instrument having a cannula with an axially-extending slot formed thereon, and which further includes a locking mechanism which prevents an endoscope or other tubular member inserted in the cannula from causing the blade to project from the cannula slot inadvertently.

It is a further object of the present invention to provide an endoscopic surgical instrument having a spring-biased blade situated in a tube that is received in the lumen of a slotted cannula, the blade being biased by the spring to be in a retracted state within the tube and selectively positionable in a projected state in which the blade protrudes from the tube and the slotted cannula when a force is applied thereto against the bias of the spring.

It is yet a further object of the present invention to provide an endoscopic surgical instrument having a retractable cutting blade and a cannula formed with an axially-extending slot from which the blade may be selectably caused to project, and which the instrument cooperates with an endoscope or arthroscope.

It is another object of the present invention to provide a surgical instrument which is attachable to an endoscope or arthroscope and having a retractable cutting blade, and which may be easily manipulated by a surgeon during a surgical procedure and used either for viewing the surgical site with the endoscope and with the blade retracted or for viewing with the endoscope while simultaneously cutting tissue with the retractable blade at the surgical site.

It is yet another object of the present invention to provide a surgical procedure using the endoscopic surgical instrument of the present invention.

In accordance with one form of the present invention, an endoscopic surgical instrument includes a main body assembly composed of several sections, and a cannula which is selectively attachable to and detachable from the main body assembly, the cannula having a bore or lumen extending axially therethrough, and an axially-extending slot formed thereon, the slot being in communication with the internal lumen of the cannula.

A tube, which houses a spring-biased retractable cutting blade assembly, is mounted on one end of the main body assembly and extends axially therefrom. The tube is receivable within the lumen of the cannula, and may be particularly oriented within the cannula lumen such that the cutting blade may be caused to project not only from the tube but also through the slot of the cannula, when such is desired by a surgeon during a surgical procedure. The inner tube has an axially-extending bore in which an endoscope or arthroscope may be received. The instrument, when mounted on the endoscope or arthroscope, may be locked in one position by a surgeon during a surgical procedure to allow the distal end of the endoscope to engage the blade assembly and cause the cutting blade to project from the inner tube and slot of the cannula during a tissue cutting procedure, or may be locked in another position to prevent the distal end of the endoscope from engaging the blade assembly so that the cutting blade remains retracted within the inner tube and without projecting therefrom or the slotted cannula.

These and other objects, features and advantages of the present invention will be apparent from the following detailed description of illustrative embodiments thereof, which is to be read in connection with the accompanying drawings.

BRIEF DESCRIPTION OF THE DRAWINGS

FIG. 21 is an exploded perspective view of the inner tube and retractable cutting blade of the surgical instrument of the present invention shown in FIG. 20.

FIG. 24 is an exploded view of the spring-biased, retractable blade assembly forming a portion of the surgical instrument of the present invention shown in FIGS. 20-23.

FIGS. 25A-25I are various views of the front section of the main body assembly forming part of the endoscopic surgical instrument of the present invention.

FIGS. 26A-26L are various views of the middle section of the main body assembly forming part of the endoscopic surgical instrument of the present invention.

FIGS. 27A-27L are various views of the rear section of the main body assembly forming part of the endoscopic surgical instrument of the present invention.

FIGS. 28A-28L are various views of the cannula forming part of the endoscopic surgical instrument of the present invention.

DETAILED DESCRIPTION OF THE PREFERRED EMBODIMENTS

Figure 1:
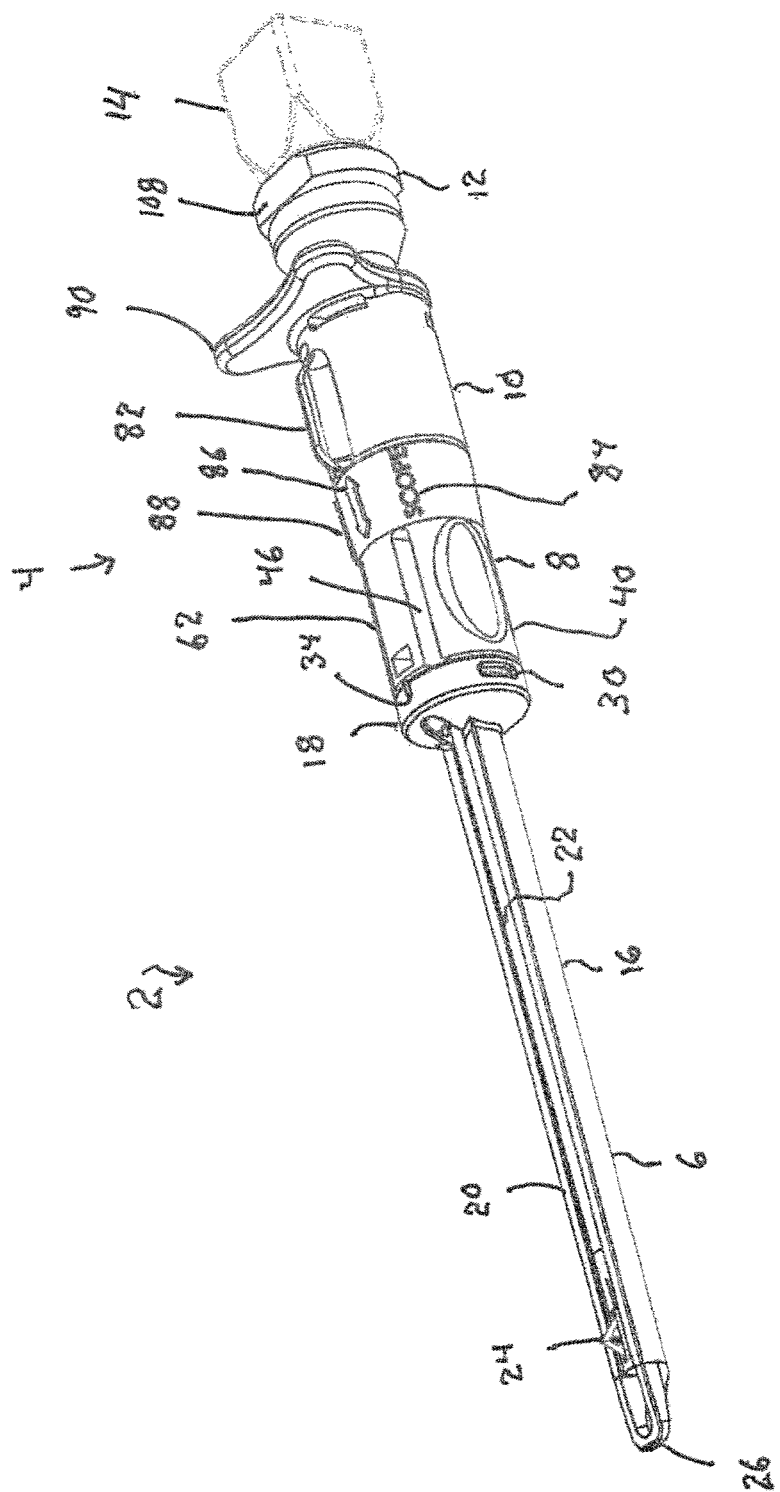
FIG. 1 is a perspective view of the endoscopic surgical instrument formed in accordance with the present invention, and illustrating a portion of an endoscope partially received by the instrument.
Figure 2:
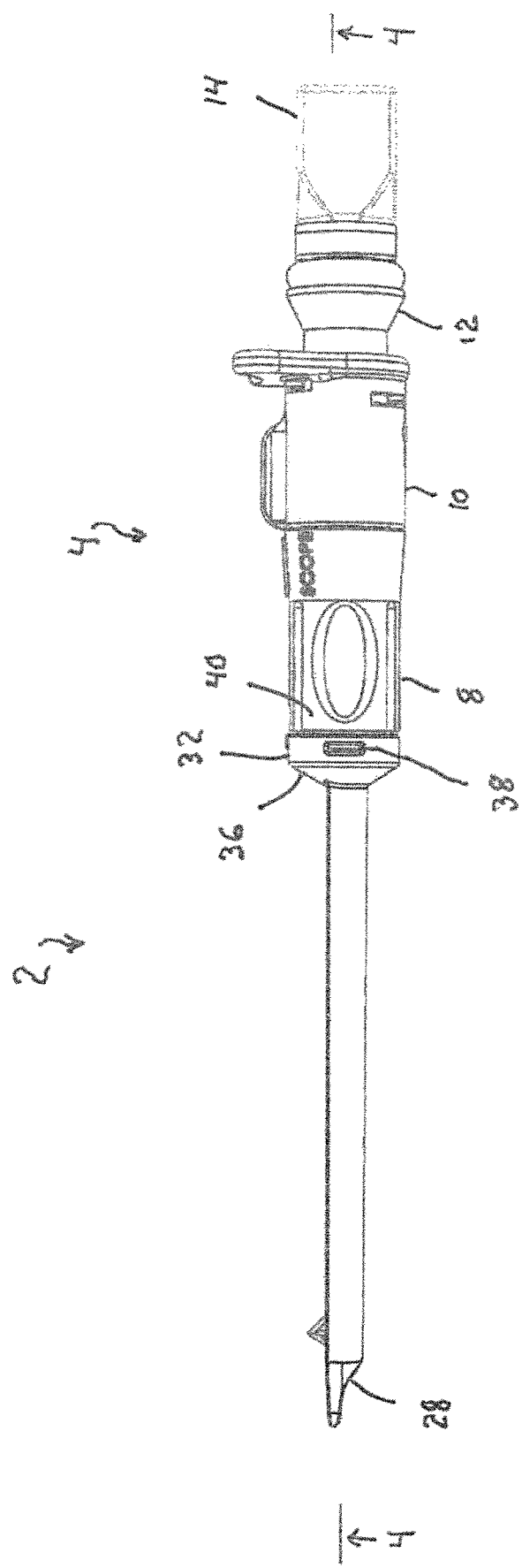
FIG. 2 is a side view of the surgical instrument of the present invention, with the attached endoscope, shown in FIG. 1.
Figure 3:
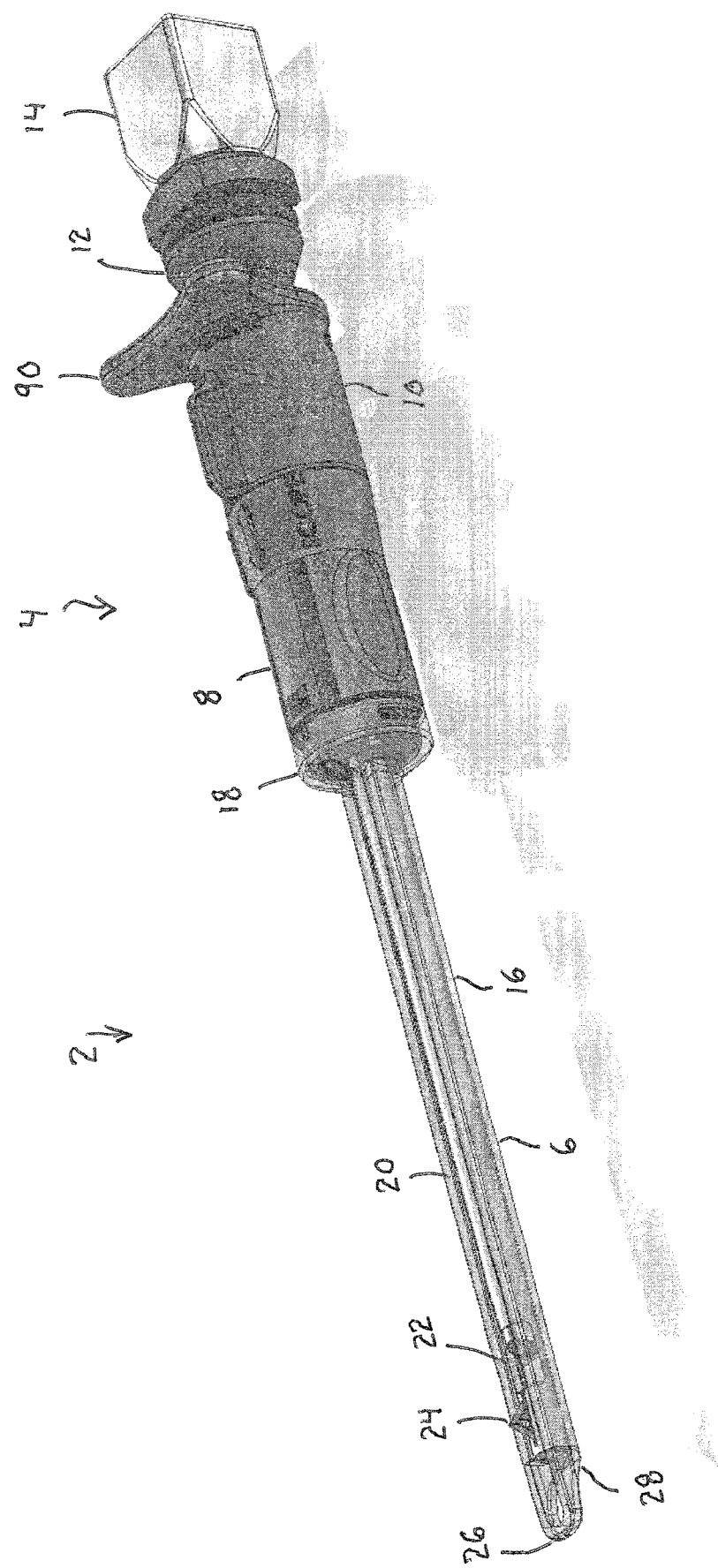
FIG. 3 is a perspective view of the surgical instrument of the present invention and endoscope partially received thereby, as shown in FIGS. 1 and 2, with the cannula of the instrument being shown as transparent to illustrate how the distal end of the endoscope causes the retractable blade of the surgical instrument to project outwardly from a slot formed in the cannula.
Figure 4:
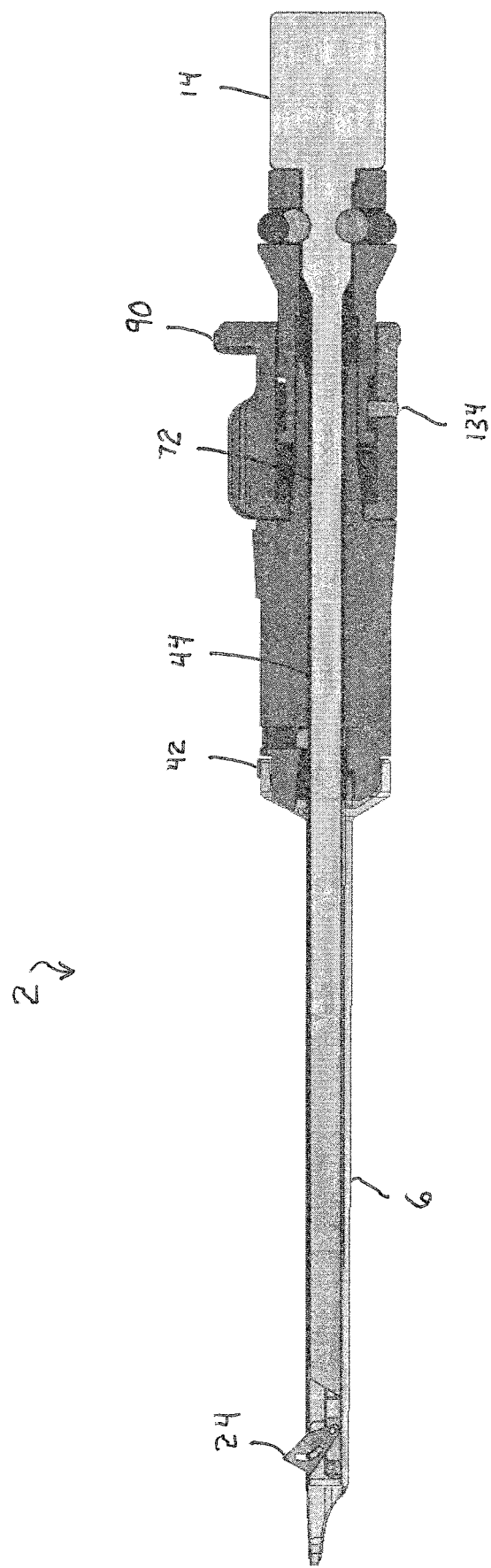
FIG. 4 is a cross-sectional view of the surgical instrument of the present invention and the endoscope shown in FIGS. 1-3, taken along line 4-4 of FIG. 2.
Figure 5:
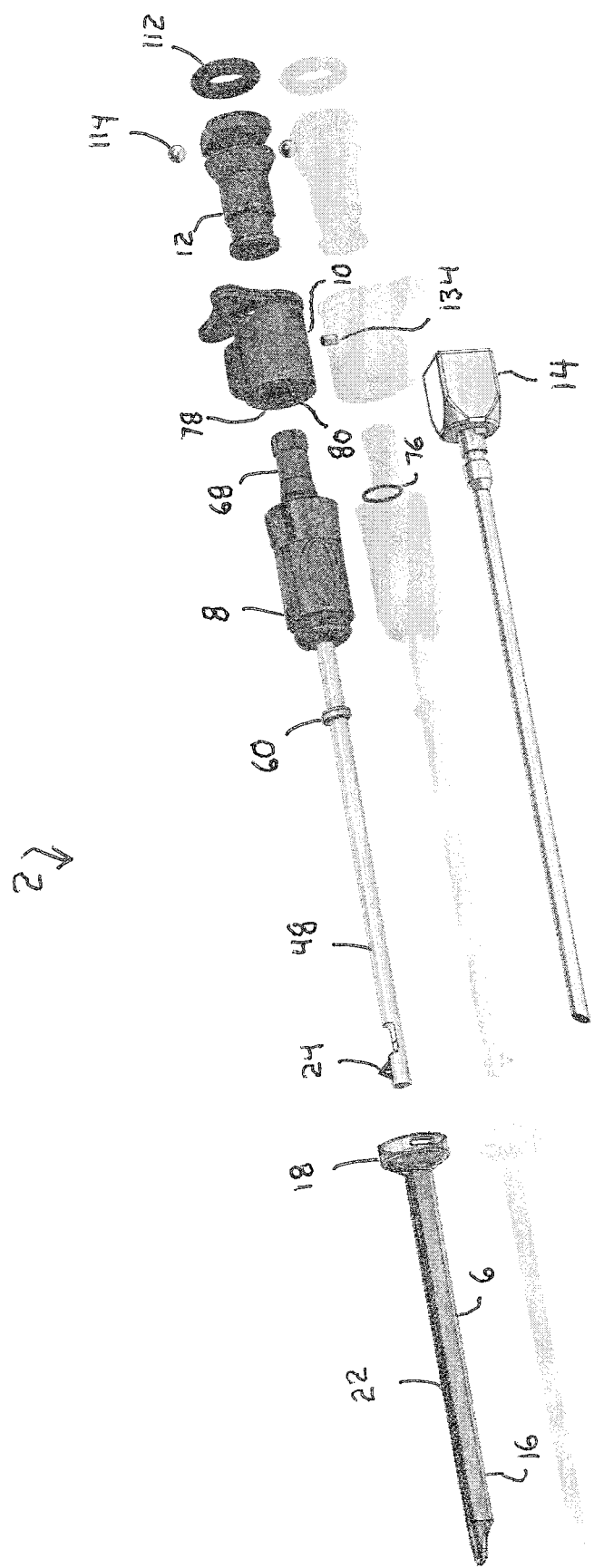
FIG. 5 is a partially exploded view of the surgical instrument of the present invention shown in FIGS. 1-4.

Referring initially to FIGS. 1-5, 10-19 and 25A-28L of the drawings, it will be seen that an endoscopic surgical instrument 2 formed in accordance with the present invention includes a main body assembly 4 and a cannula 6 mounted to the main body assembly 4. More specifically, the main body assembly 4 includes three sections, that is, a front section 8, a middle section 10 that is mounted on the front section 8 and partially rotatable thereon, and a rear section 12 mounted on the middle section 10. The cannula 6 of the surgical instrument 2 is removably attached to the front section 8 of the main body assembly 4. An endoscope or arthroscope 14 is received through the main body assembly 4 and attaches to the rear section 12 thereof, with the distal end of the endoscope extending into the cannula 6, as will be more fully described herein.

The cannula 6 of the surgical instrument 2 includes a tubular member 16 having an internal lumen that extends from an enlarged diameter (when compared to that of the tubular member), cup-shaped member 18 that attaches to the front end of the front section 8 of the main body assembly 4. The tubular member 16 of the cannula 6 includes a flattened top wall 20, and a slot 22 formed through the thickness of the flattened top wall 20 and extending axially thereon over most or at least a portion of the longitudinal length thereof. The slot 22 is provided to allow a retractable blade 24 to project therefrom, as will be explained in greater detail. Preferably, the cannula 6, and at least the tubular member 16 thereof, is transparent so that an endoscope or arthroscope 14 received by the surgical instrument 2 of the present invention and which passes through at least a portion of the lumen of the cannula 6 can view through the clear, transparent cannula 6 in preferably all rotational directions any tissue and other anatomical features at a surgical site when a surgeon is performing a procedure on a patient.

As can be seen in FIGS. 1-5 of the drawings, the distal end 26 of the cannula 6 is preferably closed and blunt, with a curved end 28, to define an obturator thereat so that the cannula 6, when being positioned at a surgical site, will minimize any injury to the tissue that the cannula 6 comes in contact with. The retractable blade 24, as can be seen in FIGS. 1-5, is positioned at the distal end 26 of the cannula 6, but slightly axially inwardly of the obturator end 26 thereof.

The cup-shaped proximate end 18 of the cannula 6 preferably includes two diametrically opposed slots or recesses 30 positioned on a cylindrical side wall 32 thereof, as well as an opening 34 formed through the thickness of a cone-shaped wall 36 interposed between the cylindrical side wall 32 and the tubular member 16 of the cannula 6. The slots 30 receive complementary-shaped protrusions 38 formed on the front end of the front section 8 of the main body assembly 4 for removably attaching and securing the cannula 6 to the front section 8 thereof. The protrusions 38 reside on the free ends of two diametrically opposed resilient members 40 forming part of the front section 8 of the main body assembly 4. The resilient members 40 may be squeezed together radially inwardly of the front section 8 so that the cup-shaped proximate end 18 of the cannula 6 may be fitted thereon, with the protrusions 38 being received by their corresponding slots 30 formed in the cup-shaped proximate end 18 of the cannula 6. The resilient members 40 of the front section 8 are biased to expand radially outwardly to secure the cannula 6 in place on the front section 8 of the main body assembly 4.

The opening 34 formed through the thickness of the conical wall 36 of the cup-shaped proximate end 18 of the cannula 6 serves two purposes. The first is that the opening 34 is formed in the conical wall 36 in communication and in alignment with the slot 22 formed in the flat top wall 20 of the tubular member 16 of the cannula 6 so that the cutting blade 24 of the surgical instrument 2 projecting from the slot 22 in the cannula 6 may be drawn from the distal end 26 to the proximate end 18 of the cannula 6 and through the opening 34 formed in the conical wall 36 of the cup-shaped proximate end 18, if such is necessary during a surgical procedure. Furthermore, the opening 34 formed in the conical wall 36 of the cup-shaped proximate end 18 of the cannula 6 is dimensioned to receive a small projection 42 formed on the front end of the front section 8 of the main body assembly 4 to ensure that the cannula 6 is properly oriented on the main body assembly 4 when it is affixed to the front section 8 thereof.

The front section 8 of the main body assembly 4 of the surgical instrument 2 has an overall generally cylindrical shape and a central bore 44 passing axially therethrough. The two resilient members 40 used to hold the cannula 6 to the main body assembly 4 reside adjacent chordally extending slots 46 to provide space for the resilient members 40 to flex inwardly on the front section 8. The front section 8 also has a tubular member (referred to herein as the inner tube 48) that extends axially outwardly from the front end thereof.

The inner tube 48 defines a bore 50 that extends axially therethrough, and has a closed distal end 52. As will be explained in greater detail, the inner tube 48 is receivable by the tubular member 16 of the cannula 6 in the lumen thereof.

In proximity to the distal end 52 of the inner tube 48, within the bore 50 thereof, is located the retractable cutting blade assembly 54. The cutting blade 24 selectively projects from and retracts into the bore 50 through a narrow slot 56 formed in the side wall of the inner tube 48. Slightly axially inwardly from the distal end 52 of the inner tube 48 is a window 58 defined by a cutaway portion of the side wall over about a 180°, or slightly greater, portion of the side wall. This window 58 is provided so that the distal end of an endoscope or arthroscope 14, which is angled at about 30°, may view through this window 58 and through the clear, transparent cannula 6 any tissue or anatomical structure of a patient at a surgical site during a surgical procedure. As will be explained in greater detail, the distal tubular portion of the endoscope 14 is received by the bore 50 of the inner tube 48 so that the viewing end thereof is positioned in proximity to the window 58 formed in the side wall of the inner tube 48.

Near the proximate end of the inner tube 48, or spaced partially axially inwardly thereof, is fixedly mounted an alignment ring 60 extending radially outwardly from the side wall of the inner tube 48. This alignment ring 60 is force fitted between two diametrically opposed legs 62 forming part of the front section 8 of the main body assembly 4. The legs 62 have radially inwardly facing walls in which are formed arcuate recesses which receive diametrically opposite sides of the alignment ring 60 to secure the proximate end of the inner tube 48 to the front section 8 of the main body assembly 4. The alignment ring 60 is fixedly positioned on the inner tube 48 at a predetermined location on the axial length thereof so that the distal portion 64 of the inner tube 48 projects axially from the front end of the front section 8 of the main body assembly 4 a predetermined distance so as to be received by and extend through most of the full axial length of the cannula lumen. A proximate end portion 66 of the inner tube 48 that extends axially beyond the alignment ring 60 passes through at least a portion of a central bore 44 formed axially through the front section 8 of the main body assembly 4.

The front section 8 of the main body assembly 4, at the rear side thereof, includes an extended, generally tubular portion 68 that projects axially therefrom. This tubular extended portion 68 includes a hexagonally-shaped free end 70 through which the central bore 44 of the front section 8 extends, the extended portion 68 of the front section 8 being received by an axial bore 72 formed centrally in the middle section 10 of the main body assembly 4, as will be explained below.

The middle section 10 of the main body assembly 4 is mounted on the extended portion 68 of the front section 8 at the rear end thereof and is at least partially rotatable on the extended portion 68 of the front section 8, which is received by the central bore 72 of the middle section 10. The middle section 10 is rotatably held in place on the front section 8. To accomplish the mounting of the middle section 10 on the front section 8, the extended portion 68 of the front section 8 includes a circumferential groove 74 formed in the side wall thereof, and a retainer ring or O-ring 76 received in the groove 74. The front end of the middle section 10 is formed as a washer-like disc 78 having a central opening 80 that leads to and communicates with the bore 72 formed through the middle section 10, the central opening 80 being particularly dimensioned to closely fit onto the extended portion 68 of the front section 8 near where the extended portion 68 projects axially from the rear end of the larger diameter portion of the front section 8, that is, between the rear end of the front section 8 and where the retainer ring or O-ring 76 is situated on the extended portion thereof. The middle section 10 is forced axially onto the extended portion 68 of the front section 8 and over the retainer ring 76 such that the retainer ring 76 holds the middle section 10 in place at the rear of the front section 8 but allows the middle section 10 to at least partially rotate thereon.

The middle section 10 of the main body assembly 4 has a generally cylindrical shape. The middle section 10 includes a switch 82 formed as a protruding tab extending radially outwardly from the outer side wall thereof. This switch 82 is movable by finger pressure and facilitates the surgeon rotating the middle section 10 on the front section 8 in at least three different positions. More specifically, the middle section 10 may be rotated about 30° in opposite directions with respect to the front section 8 of the main body assembly 4 such that the switch 82 (i.e., the protruding tab) is in alignment with first indicia 84, preferably reading the word "SCOPE" located on the cylindrical outer wall of the front section 8 adjacent to the middle section 10, when the switch 82 is in the +30° position relative to the front section 8; or in alignment with second indicia 86 (preferably a double-ended arrow) also located on the outer wall of the cylindrical portion of the front section 8, when the switch 82 is in a 0° position relative to the front section 8; or in alignment with third indicia 88 (preferably reading the word "BLADE") also located on the outer wall of the cylindrical portion of the front section 8 of the main body assembly 4, when the switch 82 on the middle section 10 is in the −30° position relative to the front section 8 of the main body assembly 4.

As will be explained in greater detail, when the switch 82 on the middle section 10 is rotated to the "SCOPE" indicia 84 on the front section 8, the distal end of an endoscope or arthroscope 14 inserted through the main body assembly 4 and bore 50 of the inner tube 48 of the surgical instrument 2 will be prevented from axially extending more than a predetermined distance in the inner tube bore 50 so as not to engage the retractable blade assembly 54 such that the retractable cutting blade 24 does not project outwardly from the slot 56 formed in the inner tube 48 and the slot 22 formed in the cannula 6. When the middle section 10 is rotated such that the switch 82 is in alignment with the word "BLADE" 88 on the front section 8, the distal end of the endoscope 14 is permitted to engage the retractable blade assembly 54 and to cause the cutting blade 24 to project through the slot 56 formed in the side wall of the inner tube 48 and the slot 22 formed in the cannula 6. When the middle section 10 is rotated such that the switch 82 is in alignment with the double arrow indicia 86 situated on the front section 8, this position of the switch 82 allows the endoscope or arthroscope 14 to move axially forward on the surgical instrument 2 and permits a transition from the "SCOPE" state of the surgical instrument 2, where the cutting blade 24 remains safely retracted within the bore 50 of the inner tube 48, to the "BLADE" state of the surgical instrument 2, where the distal end of the endoscope 14 may engage the retractable blade assembly 54 to cause the cutting blade 24 to project outwardly from the inner tube 48 and the slot 22 formed in the cannula 6.

At the rear axial end of the middle section 10 of the main body assembly 4 is located a double wing handle 90 formed as a protruding planar flange extending radially from the cylindrical outer wall of the middle section 10. This double wing handle 90 is graspable by a surgeon during a surgical procedure and facilitates not only axial movement of the endoscope 14 relative to the surgical instrument 2 as the surgical instrument 2 and endoscope 14 transition between the "SCOPE" state and the "BLADE" state, but also axial movement of the cutting blade 24 along at least a portion of the length of the cannula slot 22 when the cannula 6 is disengaged from the main body assembly 4 of the instrument 2 and properly positioned at a surgical site.

The cylindrical inner wall of the middle section 10 which defines the central bore 72 has formed near the rear end of the middle section 10 first and second pairs of diametrically opposed, arcuate notches, recesses or slots 92, 94 formed therein, each slot or recess 92, 94 extending about 30° on the inner wall. More specifically, a first set of arcuate recesses or slots 92 formed in the inner wall is located near the rear axial end of the middle section 10, and a second set of arcuate recesses or slots 94 is formed in the inner wall of the middle section 10 but more axially inwardly thereon from where the first set of arcuate recesses or slots 92 is situated. Even more specifically, the second set of arcuate slots 94 is more axially inwardly situated with respect to the location of the first set of arcuate slots 92 by about 3/16 inches. This difference in the location of the first and second sets of arcuate recesses or slots 92, 94 determines whether the distal end of the endoscope 14 received by the surgical instrument 2 of the present invention will be permitted to engage, or will be prevented from engaging, the retractable blade assembly 54. As will be explained below, each slot 92, 94 of the first and second sets can receive a corresponding tab 96 protruding from opposite sides of the outer wall of the rear section 12 of the main body assembly 4 which is received by the central bore 72 of the middle section 10.

The rear section 12 of the main body assembly 4 of the surgical instrument 2 is also generally cylindrical in shape and has a bore 98 formed axially therethrough. The rear end 100 of the rear section 12 has a larger diameter than the axially opposite front end 102, with a conically-shaped mid-portion 104 that transitions from the larger diameter rear end 100 to the smaller diameter front end 102. The rear end wall 106 of the rear section 12 may include diametrically opposite flattened sides 108 to make it easier to slip an O-ring 112 into a circular groove 110, as described in more detail below.

On the outer wall of the rear section 12, and between the rear wall 106 and the conically-shaped mid-portion 104 of the rear section 12, is located a circular groove 110 in which an O-ring 112 is received. Ball bearings 114 are received in openings 116 formed on diametrically opposite sides of the outer wall of the rear section 12 in the groove 110 and underneath the O-ring 112. Each opening 116 extends through the thickness of the outer wall so as to be in communication with the axial bore 98 formed centrally in the rear section 12. Furthermore, these openings 116 have a smaller diameter than that of each ball bearing 114 so that only a portion of each ball bearing 114 projects into the bore 98 of the rear section 12. The ball bearings 114 are held in place in their respective openings 116 and biased radially inwardly towards the central bore 98 of the rear section 12 by the O-ring 112.

Figure 6:
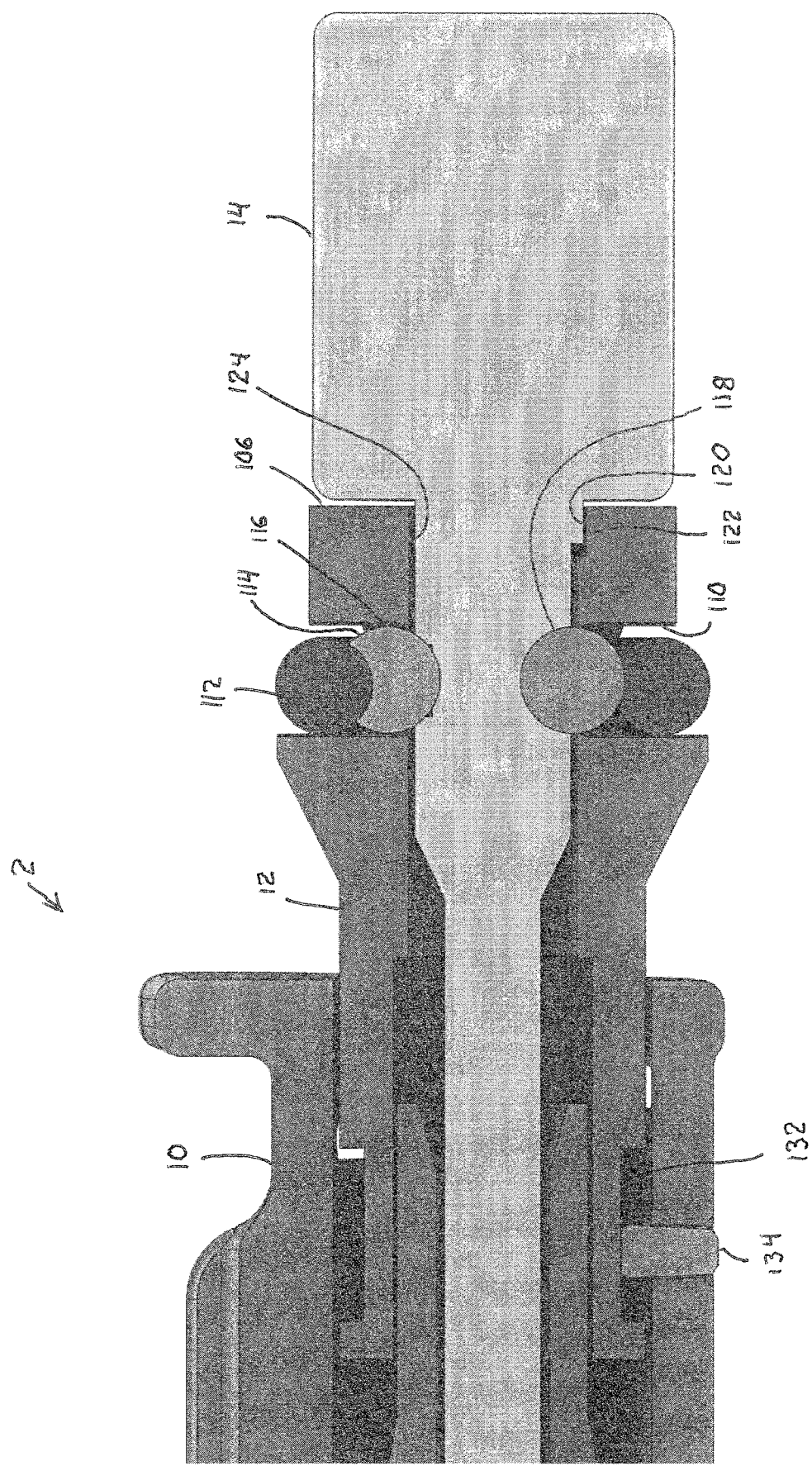
FIG. 6 is a cross-sectional view of the proximate end portion of the surgical instrument of the present invention shown in FIGS. 1-5, and further illustrating an endoscope being received thereby.
Figure 7D:
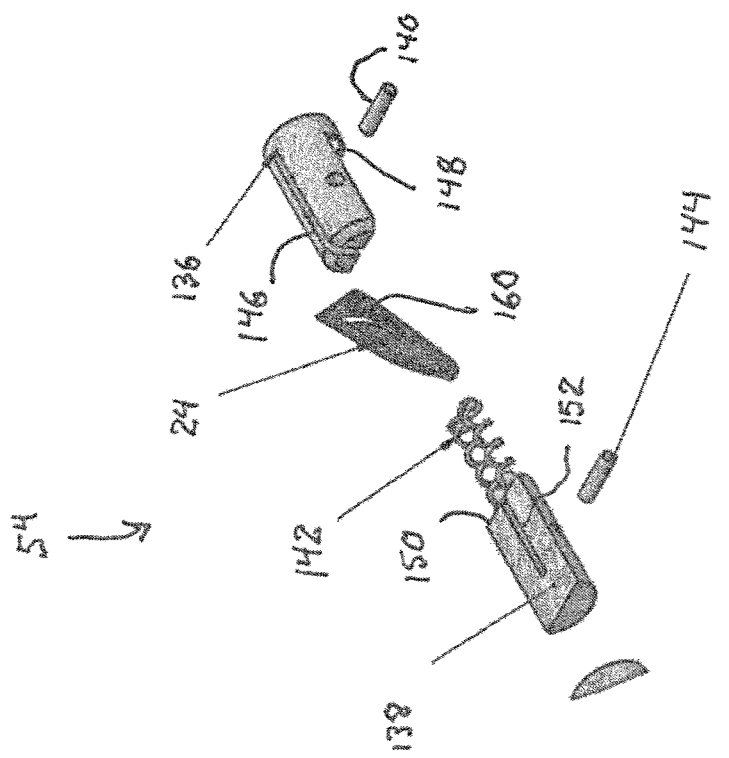
FIG. 7D is an exploded perspective view of the spring-biased, retractable blade assembly forming a portion of the surgical instrument of the present invention.
Figure 7A:
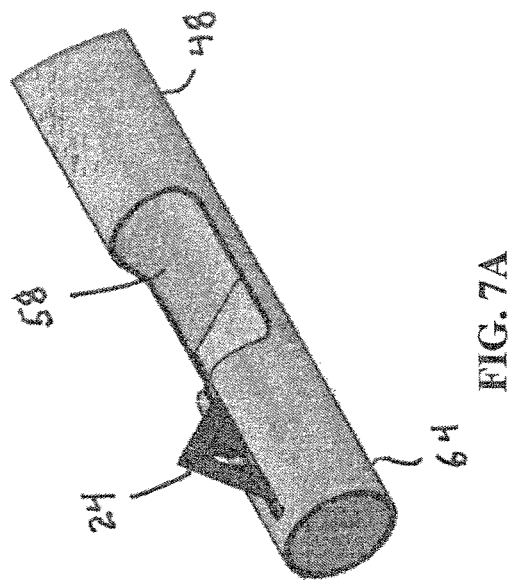
FIG. 7A is a perspective view of the inner tube and retractable cutting blade forming part of the surgical instrument of the present invention.
Figure 7B:
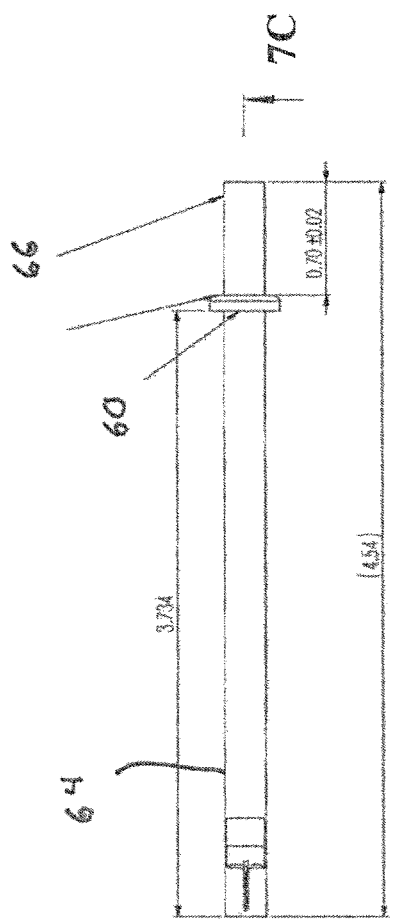
FIG. 7B a top plan view of the inner tube and retractable cutting blade forming portions of the surgical instrument of the present invention.
Figure 7C:
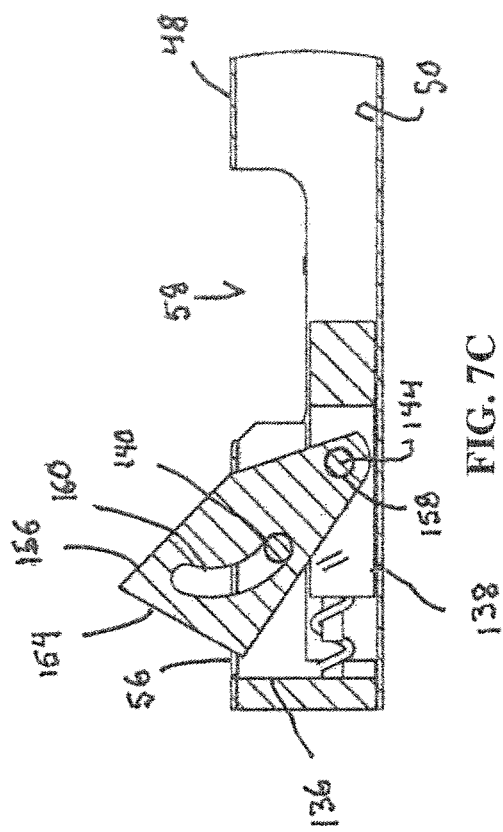
FIG. 7C is a longitudinal cross-sectional view of the distal end portion of the inner tube and cutting blade assembly forming portions of the surgical instrument of the present invention, taken along line 7C-7C of FIG. 7B.
Figure 8:
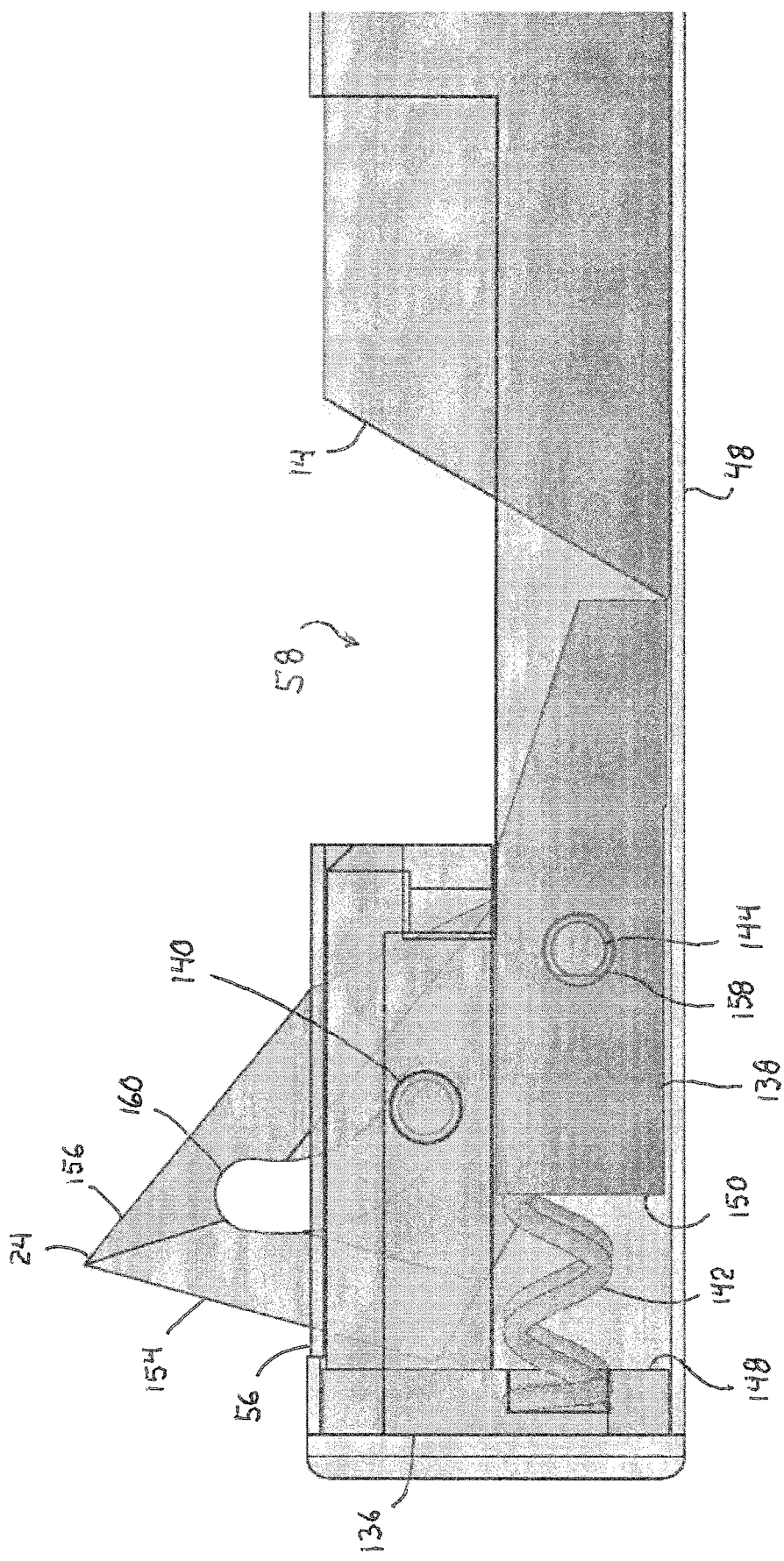
FIG. 8 is a cross-sectional view of the inner tube, shown in transparency, and the retractable blade assembly mounted therein and forming portions of the surgical instrument of the present invention.
Figure 9:
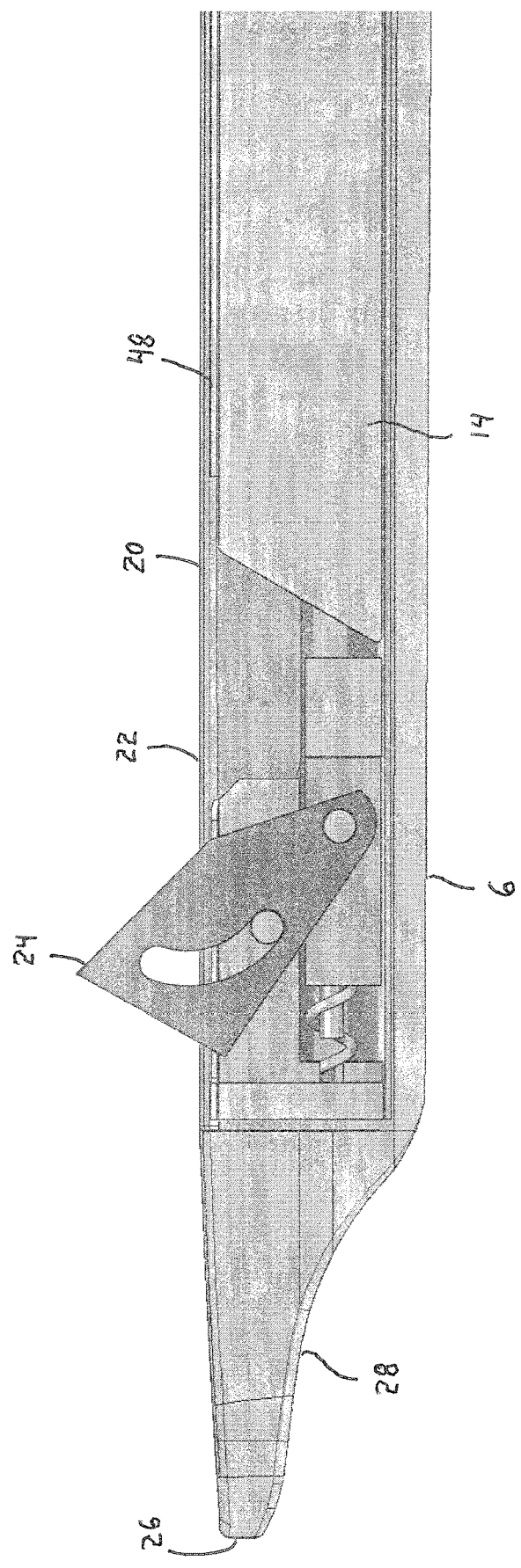
FIG. 9 is cross-sectional view of the distal end portion of the cannula of the surgical instrument of the present invention, and illustrating the inner tube and retractable blade assembly forming portions of the surgical instrument of the present invention situated therein.
Figure 10:
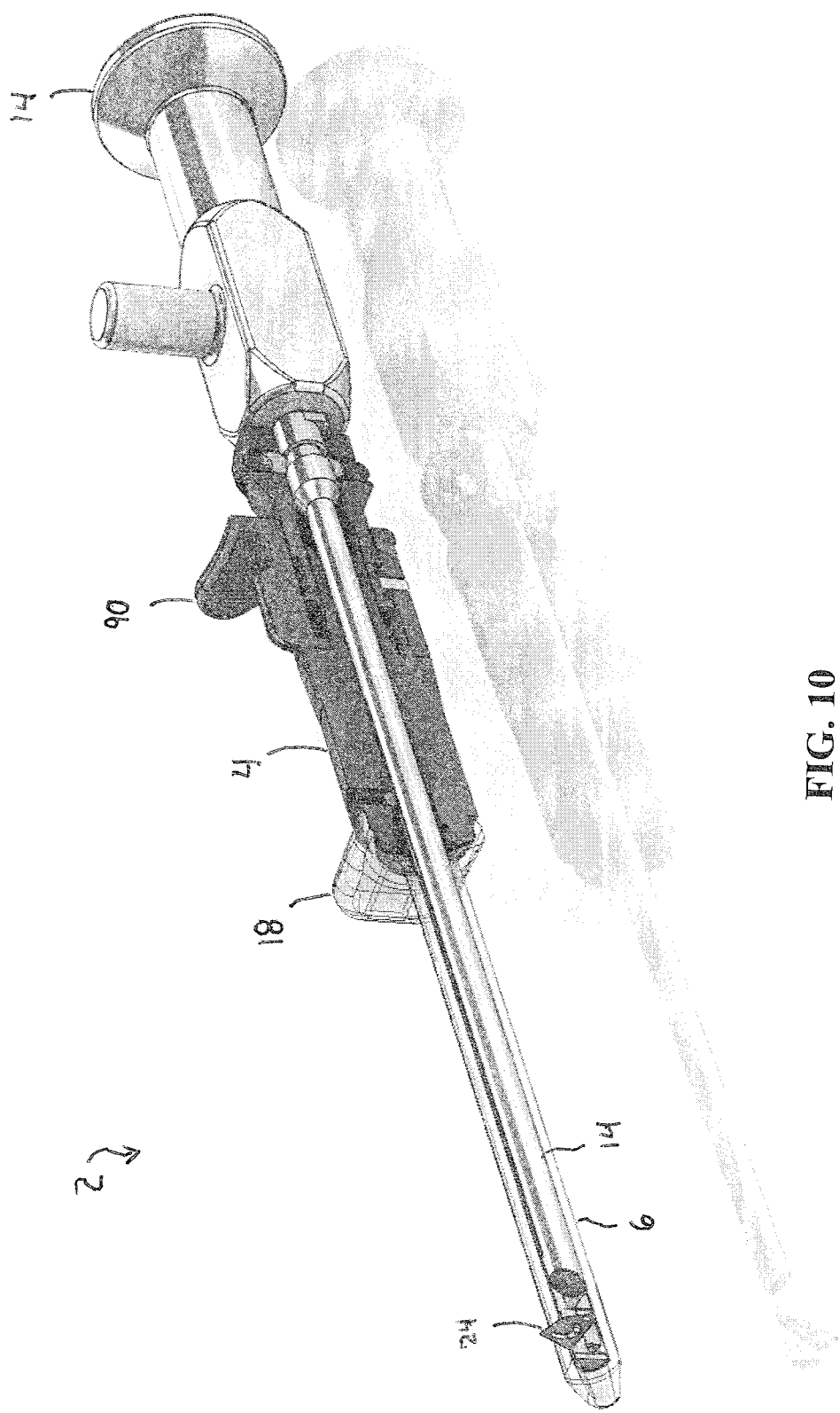
FIG. 10 is a perspective view of the surgical instrument of the present invention, shown with a portion thereof cut away, and illustrating the surgical instrument being mounted on the distal end of an endoscope.
Figure 11:
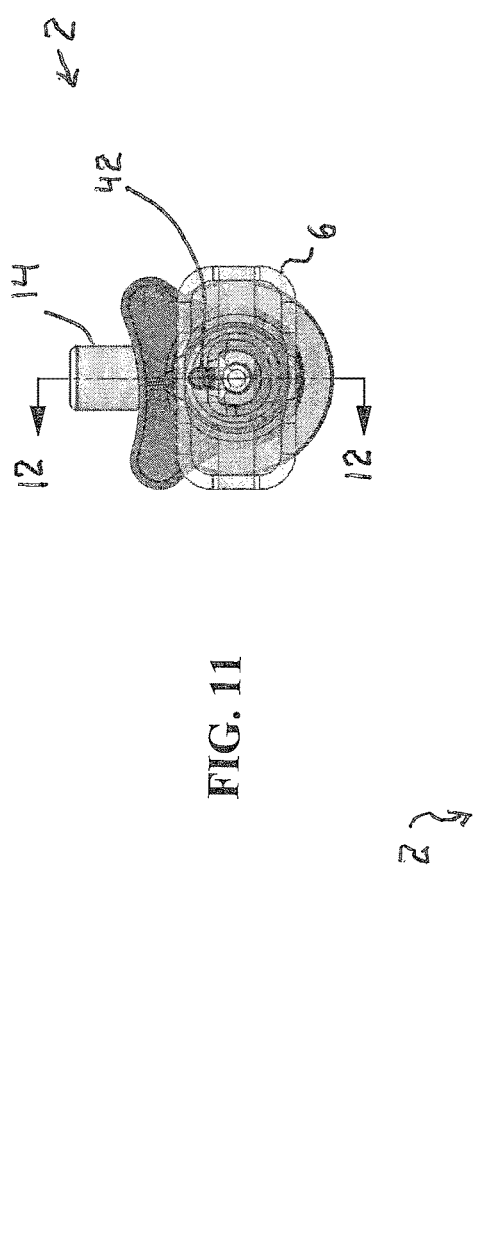
FIG. 11 is a front elevational view of the surgical instrument of the present invention and endoscope on which the surgical instrument is mounted shown in FIG. 10.
Figure 12:
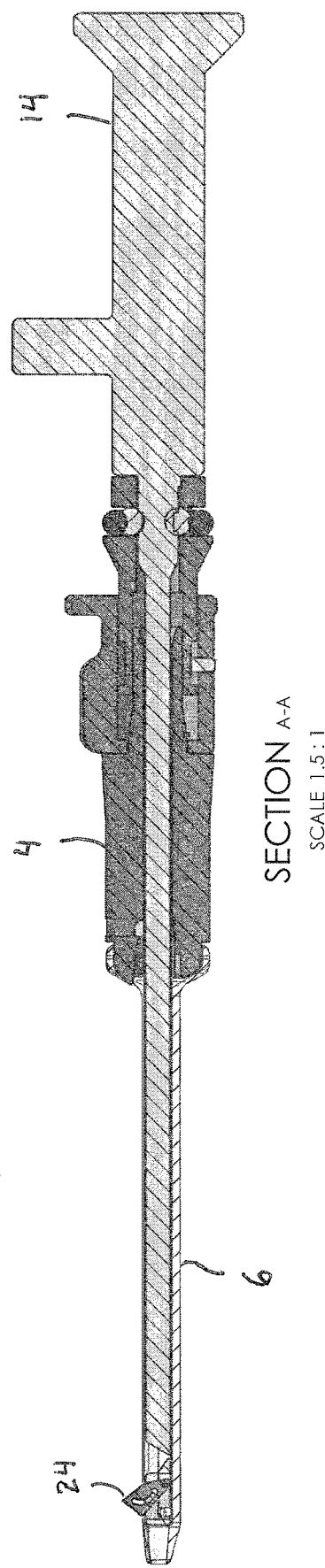
FIG. 12 is a transverse cross-sectional view of the surgical instrument of the present invention and endoscope shown in FIGS. 10 and 11, taken along line 12-12 of FIG. 11.
Figure 13:
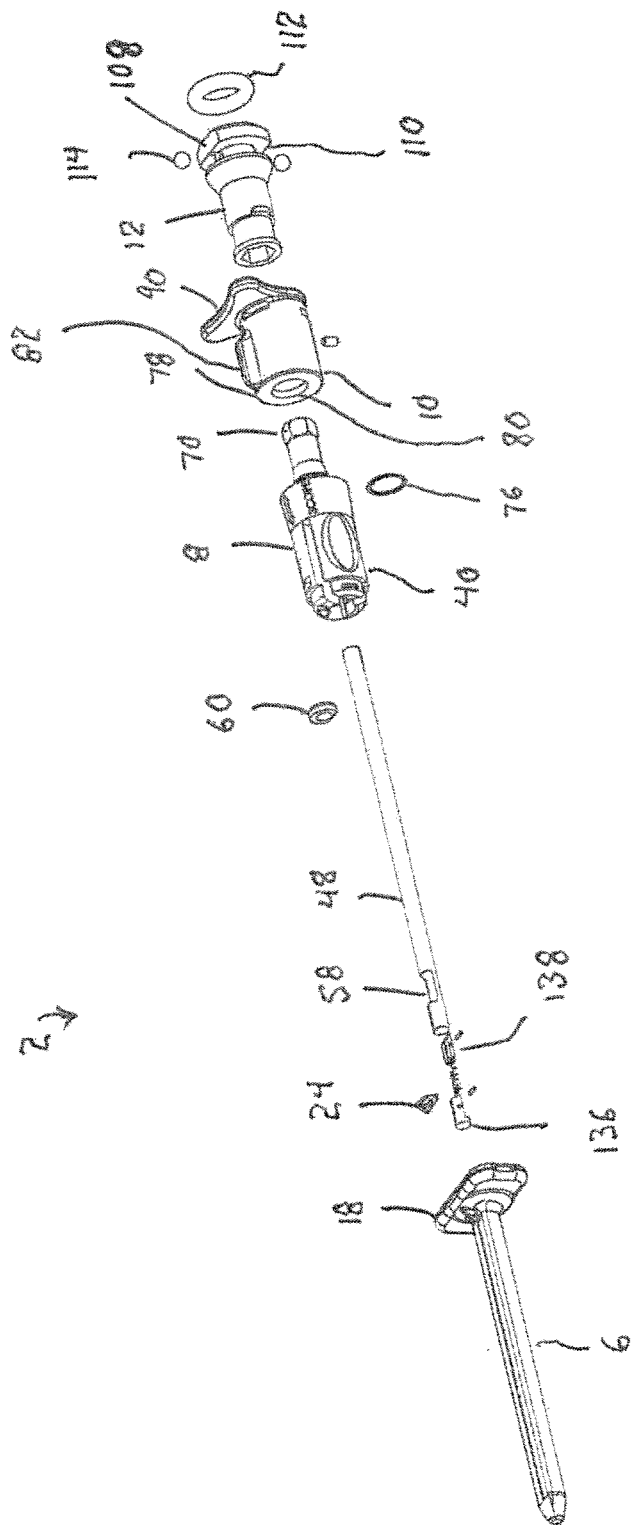
FIG. 13 is an exploded view of the surgical instrument of the present invention shown in FIGS. 10-12.
Figure 14:
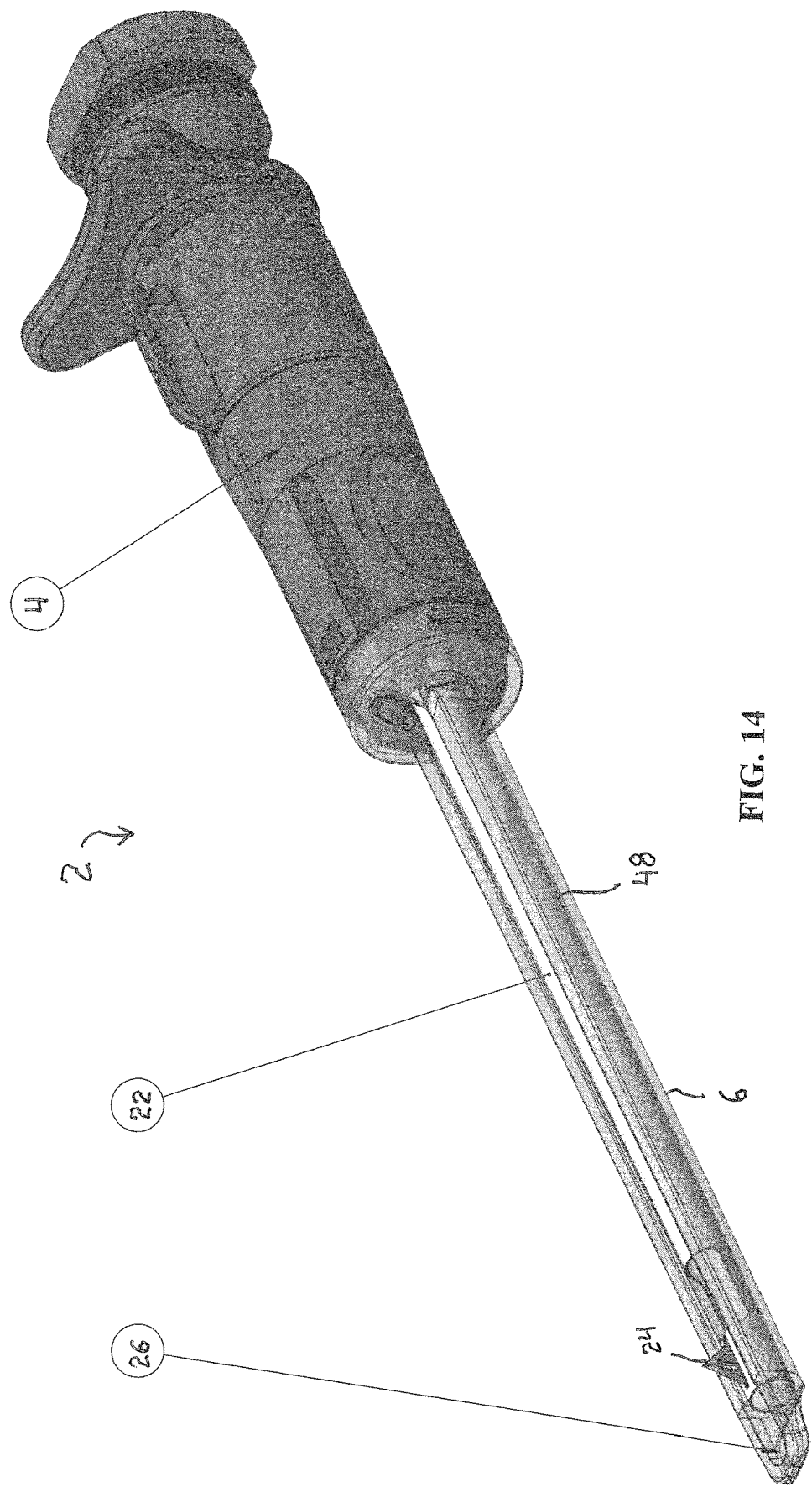
FIG. 14 is another perspective view of the endoscopic surgical instrument formed in accordance with the present invention.
Figure 15:
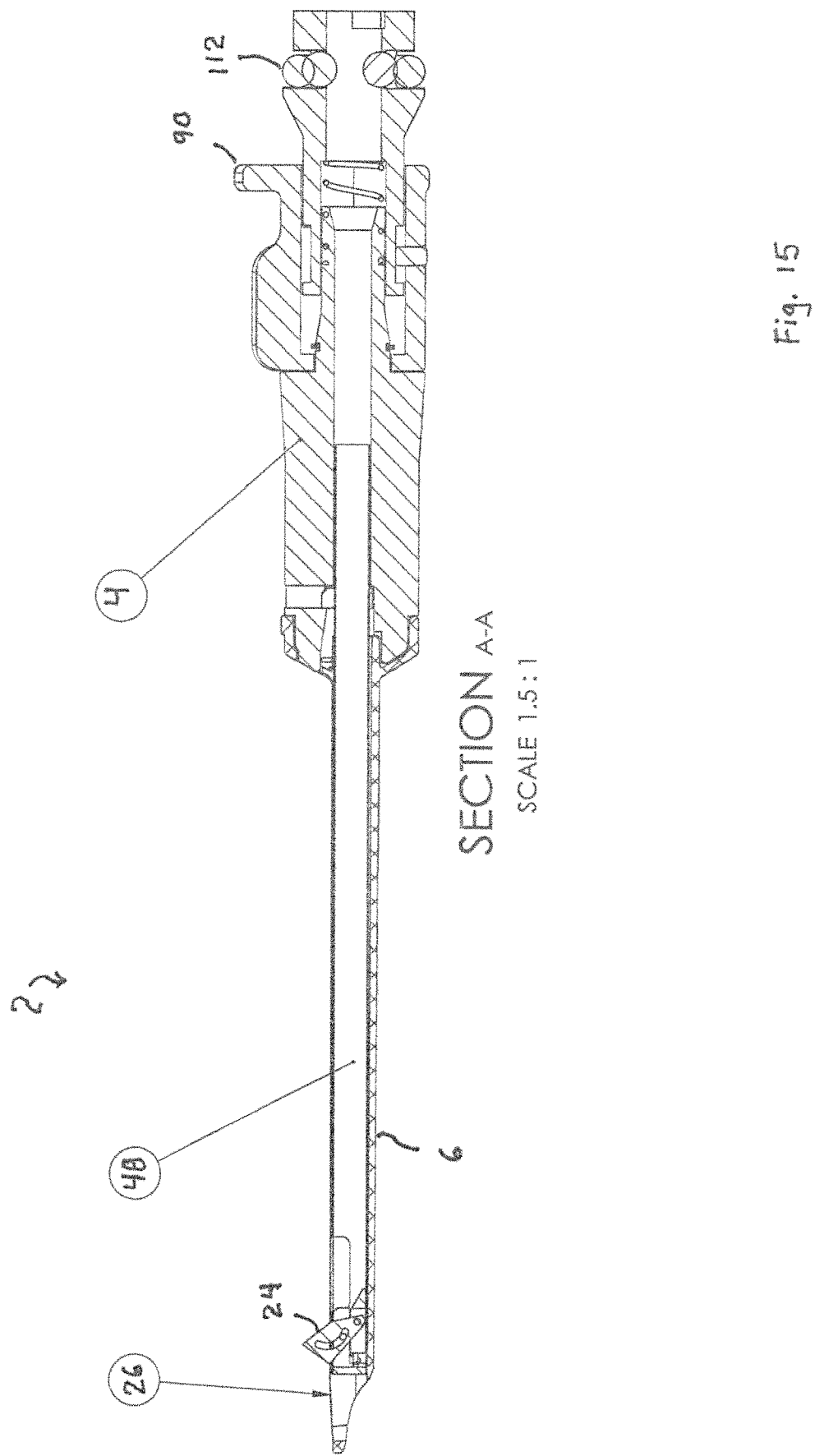
FIG. 15 is a longitudinal cross-sectional view of the endoscopic surgical instrument of the present invention shown in FIG. 14.
Figure 16:
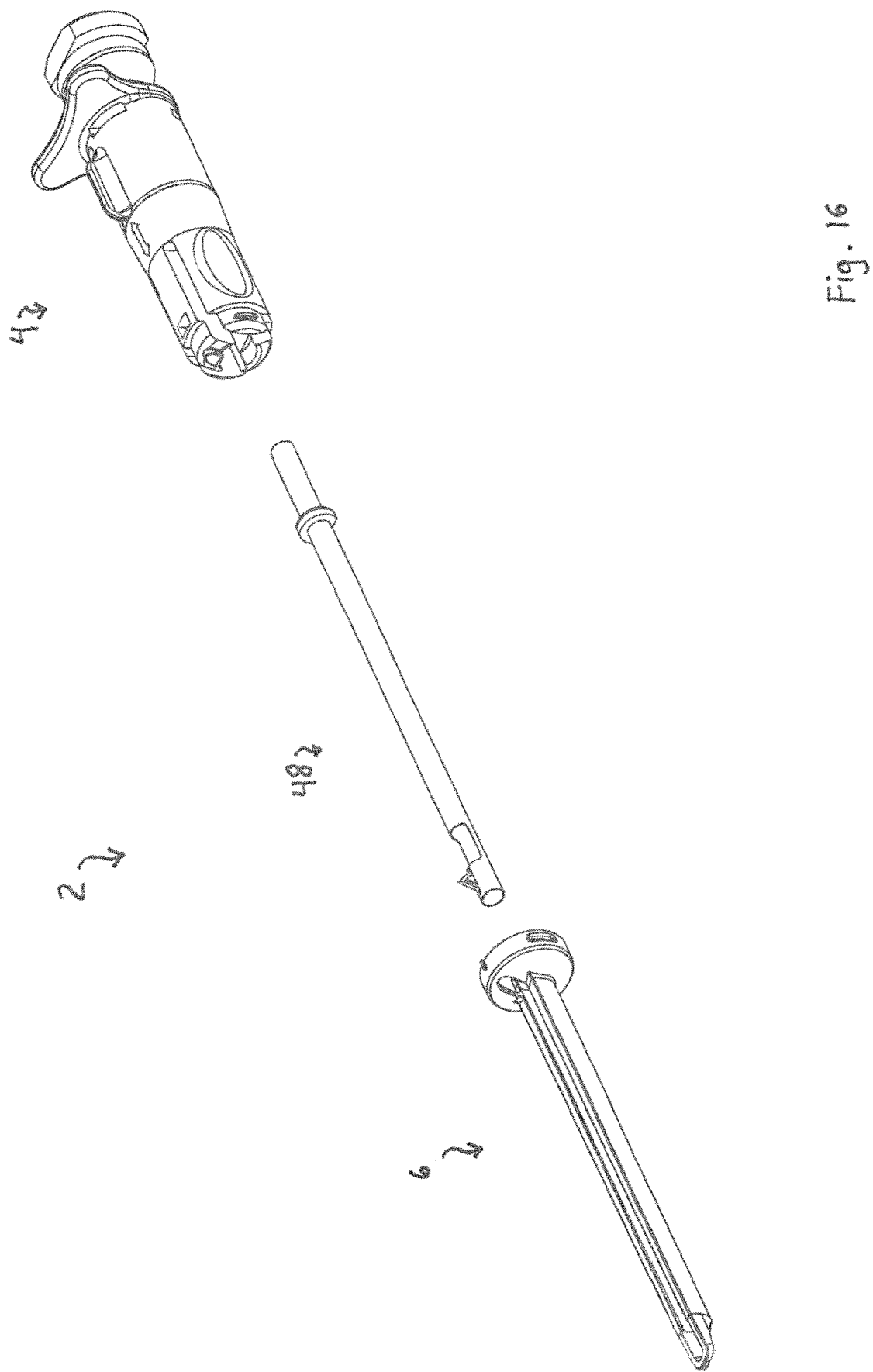
FIG. 16 is a partially exploded perspective view of the endoscopic surgical instrument of the present invention shown in FIGS. 14 and 15.
Figure 17:
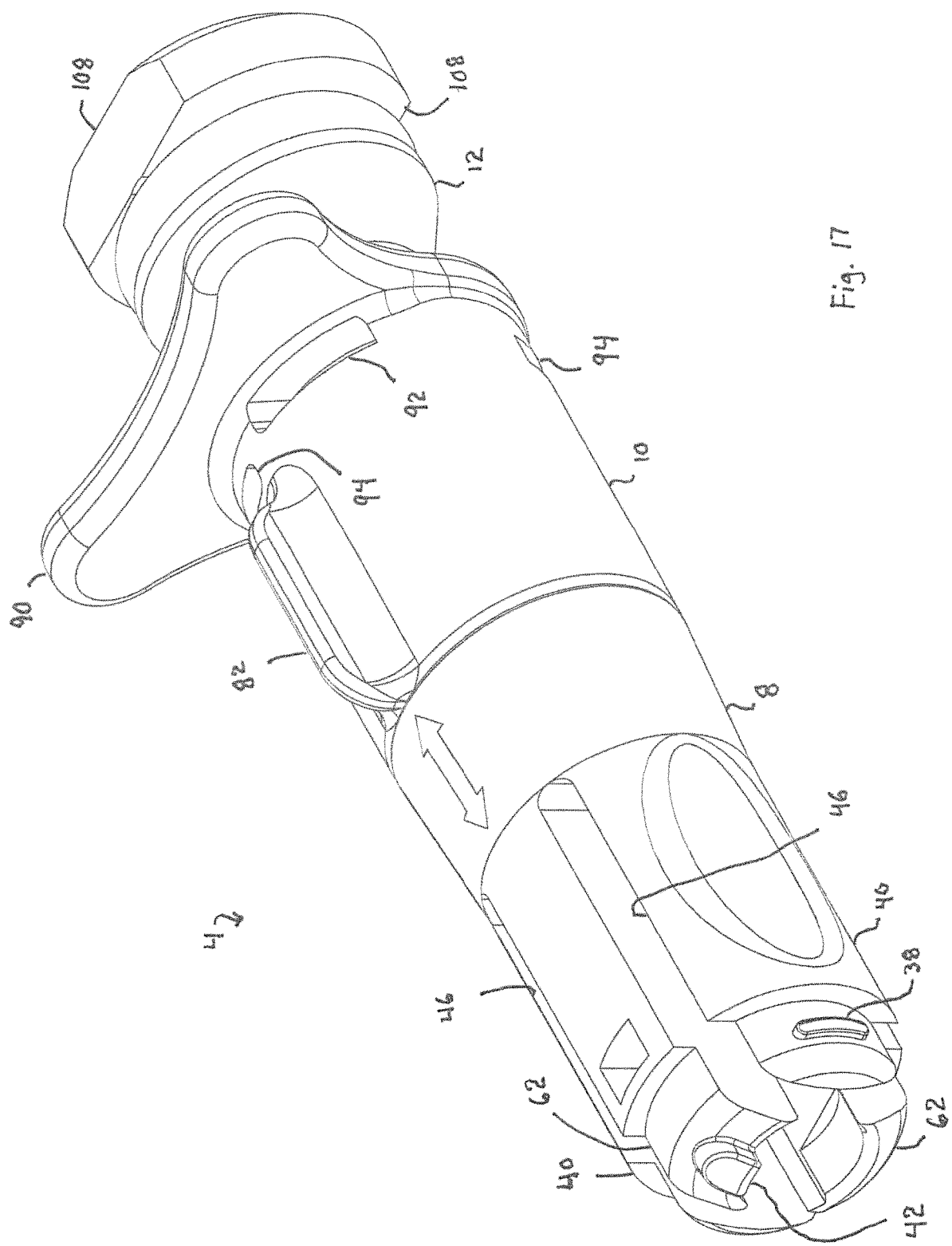
FIG. 17 is a perspective view of the main body assembly forming part of the endoscopic surgical instrument of the present invention.
Figure 18:
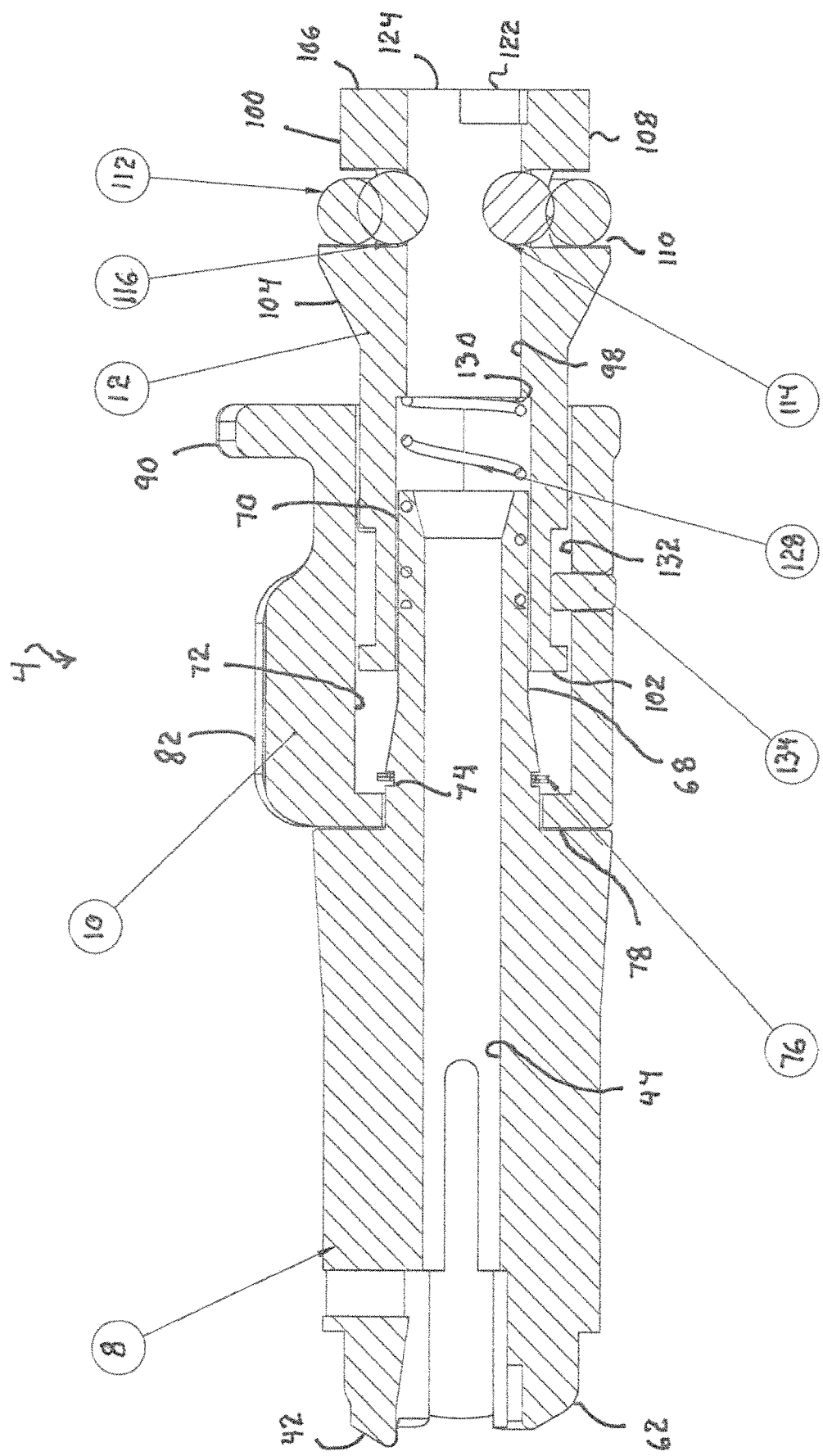
FIG. 18 is a longitudinal cross-sectional view of the main body assembly of the endoscopic surgical instrument of the present invention shown in FIG. 17.
Figure 19:
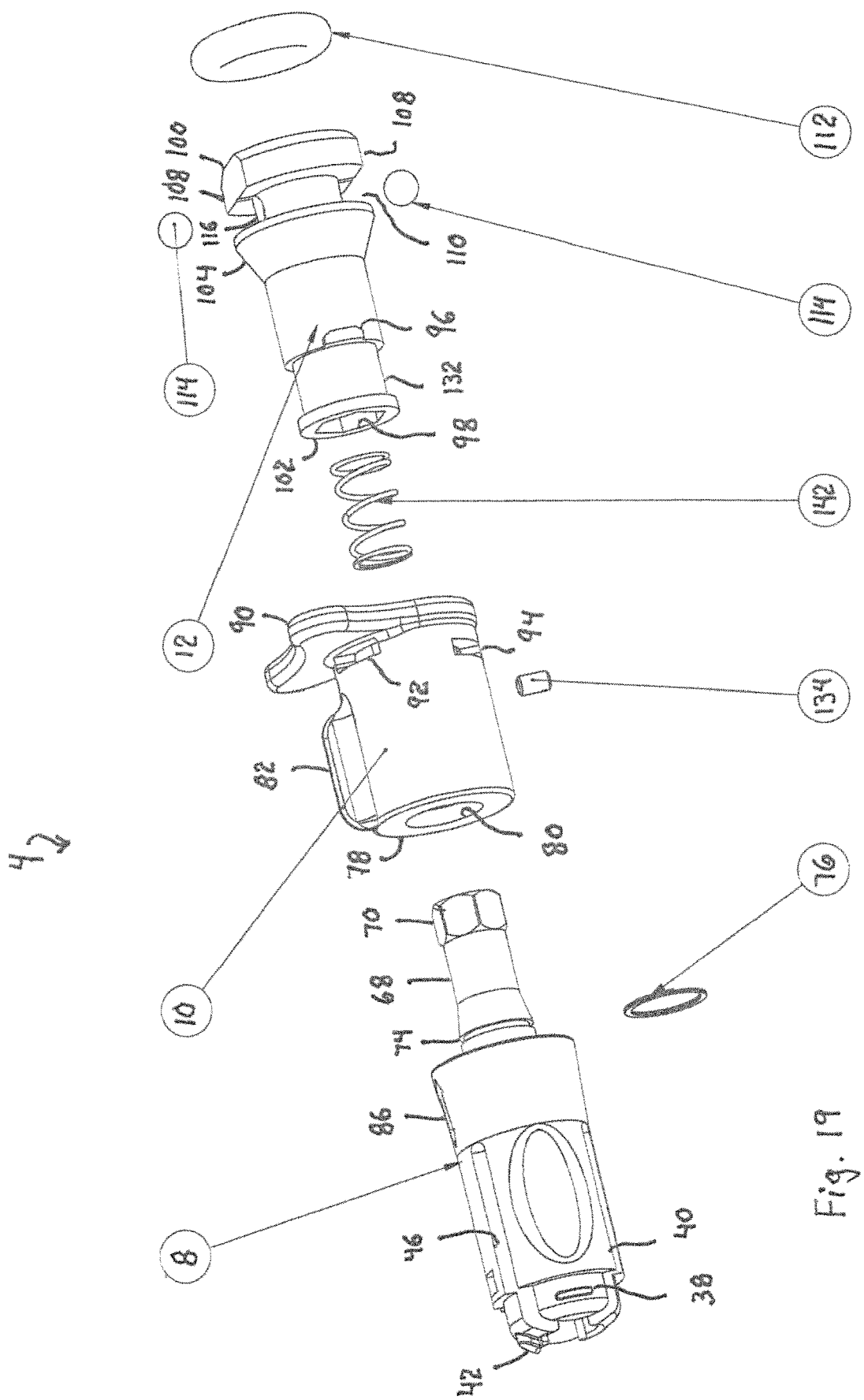
FIG. 19 is an exploded perspective view of the main body assembly of the endoscopic surgical instrument of the present invention shown in FIGS. 17 and 18.
Figure 20:
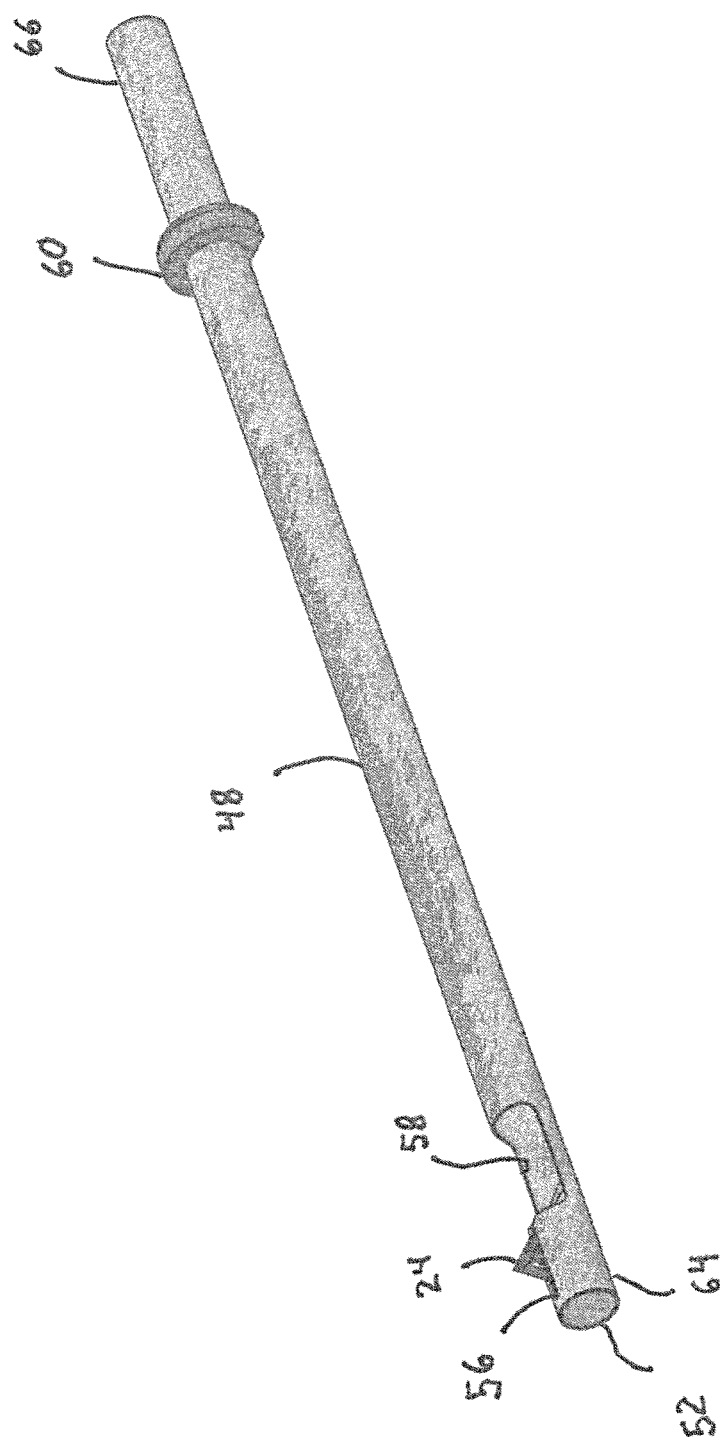
FIG. 20 is another perspective view of the inner tube and retractable cutting blade forming part of the surgical instrument of the present invention.
Figure 23:
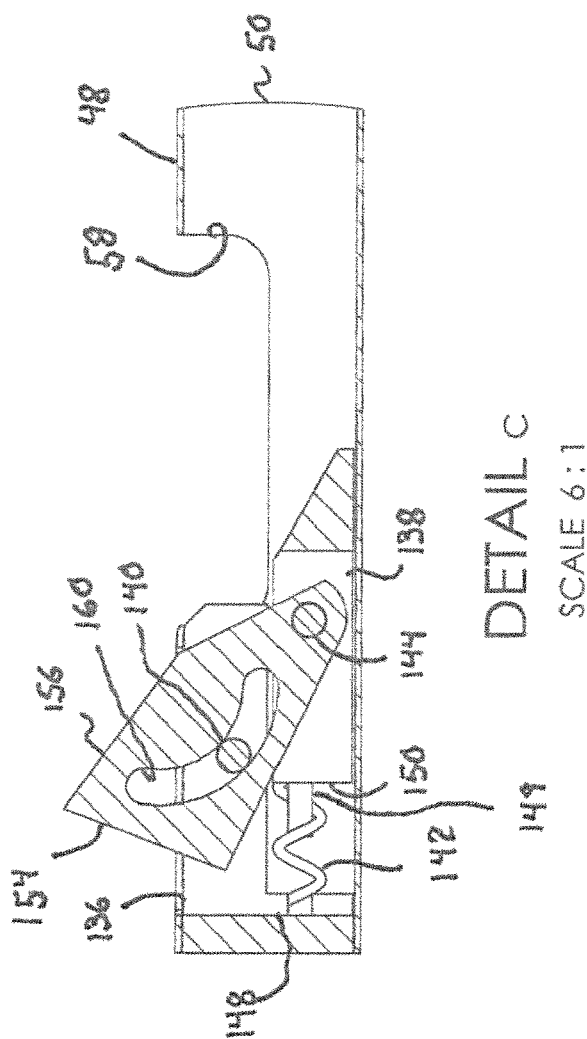
FIG. 23 is a longitudinal cross-sectional view of the distal end portion of the inner tube and cutting blade assembly of the surgical instrument of the present invention shown in FIGS. 20-22.
Figure 22:
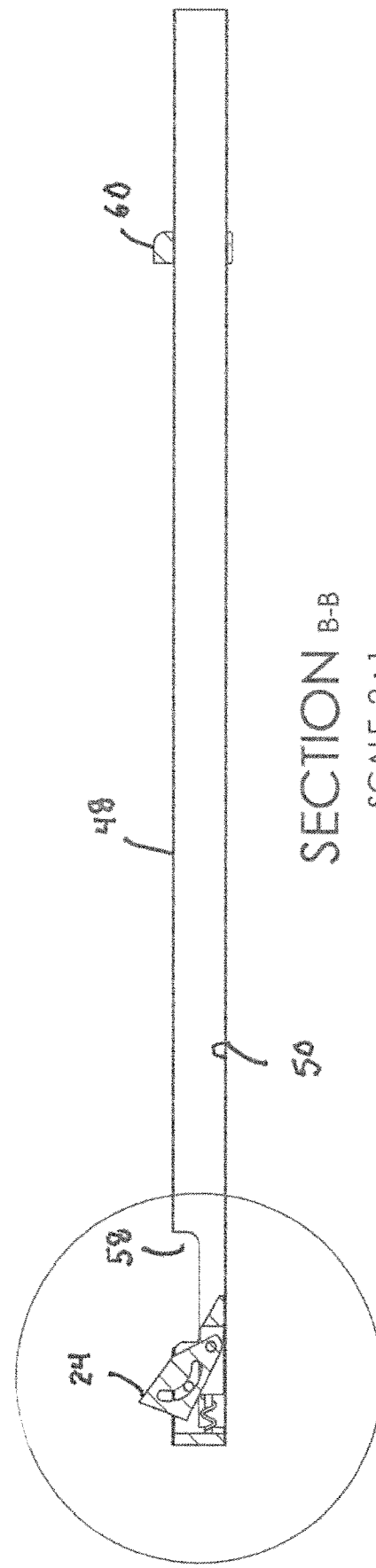
FIG. 22 is a longitudinal cross-sectional view of the inner tube and cutting blade assembly of the surgical instrument of the present invention shown in FIGS. 20 and 21.

The purpose of using the combination of a retaining O-ring 112 and ball bearings 114 is to allow an endoscope 14 to be securely retained axially on the surgical instrument 2 of the present invention until forcibly removed therefrom. As shown in FIG. 6 of the drawings, many endoscopes 14 have a circular groove 118 formed in a cylindrical outer wall thereof. When the endoscope 14 is inserted into the main body assembly 4 of the surgical instrument 2 of the present invention, the groove 118 on the endoscope 14 is aligned with the openings 116 and inwardly protruding ball bearings 114 on the rear section 12 of the main body assembly 4. The endoscope 14 is pushed axially by the surgeon into the main body assembly 4 through the central bore 98 of the rear section 12 until the ball bearings 114 come to rest in the groove 118 of the endoscope 14, locking the endoscope 14 in place within the surgical instrument 2 of the present invention. The endoscope 14 may be removed axially from the surgical instrument 2 by overcoming the force exerted thereon by the ball bearings 114 and O-ring 112 of the surgical instrument 2. Additionally, it should be noted that, preferably, one side of the groove 118 formed in the outer wall of the endoscope 14 is deeper than a diametrically opposite side of the groove 118. Furthermore, the cylindrical outer wall of the endoscope 14 is formed with a shoulder 120 at a circumferential portion thereof, which shoulder 120 may be received by a notch or flattened portion 122 of an opening 124 formed in the rear wall 106 of the rear section 12 of the main body assembly 4 to ensure that the endoscope 14 is properly oriented with respect to the surgical instrument 2 and the slot 22 formed in the cannula 6 when the endoscope 14 and surgical instrument 2 are mated together.

The two tabs 96 mentioned previously that are formed on the exterior of the rear section 12 of the main body assembly 4 are situated more towards the front end 102 of the rear section 12 and are received in either the first set of diametrically opposed arcuate recesses or slots 92 formed in the inner wall of the middle section 10, or the more axially inwardly situated second set of diametrically opposed arcuate recesses or slots 94 formed in the inner wall of the middle section 10. The tabs 96 are received in axially extending, diametrically opposed grooves 126 formed in the inner wall of the middle section 10 at the rear wall 106 thereof, the grooves 126 leading to and communicating with the first set of arcuate recesses or slots 92 and the second set of arcuate recesses or slots 94, the tabs 96 being received in either set of recesses or slots 92, 94 depending upon how far the rear section 12 is pushed into the middle section 10 and which way the middle section 10 is rotated on the front section 8 and the rear section 12 of the main body assembly 4. The axial bore 98 formed in the rear section 12 receives a compression spring 128, one axial end thereof resting against a decreased diameter seat 130 formed in the bore 98 of the rear section 12. The other axial end of the compression spring 128 engages the hexagonal end face of the extended portion 68 of the front section 8, which extended portion 68 is received within the bore 98 of the rear section 12 at the front end portion 102 thereof. The inner wall of the front end portion 102 of the rear section 12 which defines the axial bore 98 therein is also hexagonally shaped to receive the hexagonally-shaped extended portion 68 of the front section 8 so that the hexagonal end of the extended portion 68 of the front section 8 is closely received by the hexagonal bore 98 of the rear section 12 to join the front and rear sections 8, 12 together but allowing relative axial movement between the two sections 8, 12.

The front end portion 102 of the rear section 12 of the main body assembly 4 includes a cylindrical, relatively wide, groove 132 of decreased diameter formed in the outer wall thereof. This groove 132 has an axial length sufficient to allow relative axial movement between the rear section 12 and the front section 8 of the main body assembly 4 so that the tabs 96 may transition between and may be received by either the first set of recesses or slots 92 formed in the middle section 10 or the second set of recesses or slots 94. The middle section 10, mounted on the extended portion 68 of the front section 8, can rotate at least partially with respect to the front section 8 and the rear section 12.

The compression spring 128, captively retained within the bore 98 of the rear section 12 of the main body assembly 4, biases the rear section 12 axially outwardly from the middle section 10 so that the endoscope 14 received by the surgical instrument 2 of the present invention does not inadvertently engage the retractable blade assembly 54 and cause the cutting blade 24 to project through the slot 22 of the cannula 6. A pin 134 is received in a radially extending opening formed through the thickness of the outer wall of the middle section 10 and into the bore 72 thereof, and is received within the relatively wide groove 132 formed in the outer side wall of the rear section 12 of the main body assembly 4. The pin 134 thus retains the rear section 12 to the middle section 10 and, indirectly, to the front section 8, but allows axial and rotatable partial movement between the middle section 10 and the rear section 12, in order to allow the tabs 96 on the rear section 12 to transition between the first set of grooves or slots 92 and the second set of grooves or slots 94 formed on the middle section 10.

The retractable blade assembly 54 will now be described, and reference should be had to FIGS. 7A-D, 8, 9 and 20-24 of the drawings. The retractable blade assembly 54 is positioned at the distal end 52 of the inner tube 48 and forms a closure at the open end of the tube 48. The retractable blade assembly 54 includes a top blade housing 136, a bottom blade housing 138, an actuator pin 140, a retractable cutting blade 24, a compression spring 142 and a pivot pin 144.

More specifically, and as shown in FIGS. 7A-D and 20-24 of the drawings, the top blade housing 136 is situated at the distal end 52 of the inner tube 48, as mentioned previously, and closes the end of the tube 48. Thus, the top blade housing 136 is fixedly mounted in the inner tube 48. The top blade housing 136 includes a slot 146 formed through the thickness thereof through which the cutting blade 24 may extend from and retract into. This slot 146 in the top blade housing 136 is positioned to be in alignment with a similar slot 56 formed through the thickness of the outer wall of the inner tube 48 so that the blade 24 may project from and retract into both slots 146, 56.

The bottom blade housing 138 slides reciprocatingly in the bore 50 of the inner tube 48 and at least partially under the top blade housing 136. The bottom blade housing 138 is slidably joined to the top blade housing 136 by one or two compression springs 142, one axial end of each of which is connected to a shoulder 148 of the top blade housing 136, and the opposite axial end of each of which is mounted on a respective retaining post 149 extending outwardly from an end wall 150 of the bottom blade housing 138 that faces the shoulder 148 of the top blade housing 136. The bottom blade housing 138 also includes a slot 152 formed in an upper surface thereof, which slot 152 is positioned to be in alignment with the slot 146 of the top blade housing 136. The slot 152 in the bottom blade housing 138 also at least partially receives a portion of the cutting blade 24, as will be described below.

There is a pivot pin 144 that passes transversely through the body of the bottom blade housing 138. This pivot pin 144 holds one end of the cutting blade 24 in place in the slot 152 of the bottom blade housing 138, and allows the cutting blade 24 to pivot thereon and within the slot 152. Similarly, there is an actuator pin 140 which passes transversely through the top blade housing 136 and through the slot 146 formed therein.

The retractable cutting blade 24 includes a forward facing sharpened edge 154 and a rearward facing sharpened edge 156. The blade 24 also includes an opening 158 formed transversely therethrough located generally opposite the cutting edges 154, 156 and at a lower portion of the blade 24. This opening 158 receives the pivot pin 144 of the bottom blade housing 138, and the pivot pin 144 secures the blade 24 to the bottom blade housing 138 but allowing it to pivot thereon.

The retractable cutting blade 24 further includes an arcuate slot 160 formed through the thickness thereof and at an upper portion thereof, nearer the sharpened edges 154, 156 than where the pivot pin opening 158 is located. This arcuate slot 160 is provided for receiving the actuator pin 140 that passes through the top blade housing 136. The actuator pin 140, when received by this arcuate slot 160 formed in the cutting blade 24, causes the cutting blade 24 to move within the slot 146 of the top blade housing 136 between an extended position (when the actuator pin 140 is at or near the bottom end of the arcuate slot 160) and a retracted position (when the actuator pin 140 is located at or near the upper end of the arcuate slot 160).

The compression spring 142 biases the bottom blade housing 138 away from the top blade housing 136. When pressure is exerted on the bottom blade housing 138 by the tip of an endoscope or arthroscope 14 to compress the spring 142, the bottom blade housing 138 moves forward, towards the top blade housing 136. As a result, the cutting blade 24 pivots on the pivot pin 144 of the bottom blade housing 138 and is guided in its movement by the actuator pin 140 situated within the arcuate slot 160 formed therein. Since the top blade housing 136 is fixed within the inner tube 48, movement of the bottom blade housing 138 towards the top blade housing 136 causes the cutting blade 24 to move from a retracted state, with the actuator pin 140 being situated at or near the upper end of the arcuate slot 160 formed in the blade 24, to an extended state, with the actuator pin 140 being located at or near the lower end of the arcuate slot 160 formed through the blade 24, such that the blade 24 extends outwardly of the slot 146 formed in the top blade housing 136 as well as the aligned slot 56 formed in the inner tube 48.

When the tip of the endoscope or arthroscope 14 is withdrawn in the inner tube 48, the compression spring 142 relaxes and causes the bottom blade housing 138 to move away from the top blade housing 136, resulting in the cutting blade 24 being retracted within the slot 146 formed in the top blade housing 136 and the slot 56 formed in the inner tube 48, due to the blade 24 pivoting on the pivot pin 144 and being affixed to the slidable bottom blade housing 138, and with the actuator pin 140 now occupying the top end of the arcuate slot 160 formed in the cutting blade 24. Accordingly, the retraction and extension of the cutting blade 24 through the slot 56 in the inner tube 48 and the slot 22 of the cannula 6 may be easily controlled by the surgeon at any time during a surgical procedure by how far the tip of the endoscope 14 extends into the inner tube 48 of the surgical instrument 2.

More specifically, the surgeon may easily control the extent to which the distal end or tip of the endoscope or arthroscope 14 extends into the inner tube 48 of the surgical instrument 2 by locating the switch 82 on the middle section 10 of the main body assembly 4 in the "SCOPE" position or the "BLADE" position. Even more specifically, when the surgical instrument 2 is in the "SCOPE" position, an endoscope or arthroscope 14 received by the surgical instrument 2 will not extend into the inner tube 48 so far as to actuate the retractable blade assembly 54 and, accordingly, the cutting blade 24 will remain in a retracted position within the inner tube 48. However, by rotating the switch 82 on the main body assembly 4 to the "BLADE" position, the tip or distal end of the endoscope or arthroscope 14 will now engage the retractable blade assembly 54 and, in particular, cause the bottom blade housing 138 to slide against the bias of the compression spring 142 towards the top blade housing 136, causing the cutting blade 24 to extend upwardly through the slot 56 of the inner tube 48 and the slot 22 of the outer cannula 6 to effect the cutting of tissue during a surgical procedure.

A surgical procedure using the endoscopic surgical instrument 2 of the present invention will now be described. By way of example only, the surgical procedure described herein relates to treatment of a patient afflicted with carpel tunnel syndrome in which the flexor retinaculum or transverse carpal ligament is severed in the surgical procedure.

An incision is made just proximal or distal to the transverse carpal ligament, making an entry portal. The distal end 26 of the cannula 6, attached to the surgical instrument 2 or another instrument, such as an endoscope or arthroscope 14, is inserted into the entry portal, and the front edge of the cannula 6 is introduced into the incision and used to create a passage under the carpal transverse ligament, but superficial to the median nerve, with the slot 22 of the cannula 6 facing the transverse carpal ligament. The procedure is observed with the optical system of the endoscope 14. The optical system is moved axially or rotated within the transparent cannula 6, when detached from the surgical instrument 2, to observe and image the target tissue and surrounding tissues. The distal end of the endoscope or arthroscope 14, received by the inner tube 48 of the surgical instrument 2, may view such tissue through the window 58 formed in the inner tube 48, without actuating the retractable blade assembly 54 so that the cutting blade 24 remains retracted within the inner tube 48 of the surgical instrument 2.

The instrument 2, during this procedure of observation of the tissue at the surgical site, is in the "SCOPE" mode to prevent the distal end or tip of the endoscope 14 from inadvertently actuating the retractable blade assembly 54. Also, during this tissue visualization step in the surgical procedure, the transparent cannula 6 may be released from the main body assembly 4 of the surgical instrument 2 by squeezing the diametrically opposed resilient members 40 of the front section 8 together so that the distal end of the endoscope 14 may be rotated within the disassociated cannula 6 and moved axially therein to view all aspects of the surrounding tissue at the surgical site. The optical system of the endoscope 14 is used to visualize not only the transverse carpal ligament but also all surrounding tissue and the location of the median nerve. It should be noted that the slot 22 of the transparent cannula 6, formed on the flat top wall 20 thereof, will remain positioned in alignment to face the transverse carpal ligament and will be in proper position when the blade 24 is extended from the cannula slot 22.

After the visualization step has been performed, as described above, the inner tube 48 of the surgical instrument 2 is repositioned in the cannula 6 such that the blade slot 56 of the inner tube 48 is aligned with the slot 22 formed in the cannula 6 so that the cutting blade 24, when the retractable blade assembly 54 is actuated, will project through both slots 56, 22. The surgical instrument 2 is now switched by the surgeon to the "BLADE" position on the main body assembly 4 thereof. This causes the distal end of the endoscope 14 to engage the retractable blade assembly 54, causing the cutting blade 24 to project outwardly not only from the slot 56 in the inner tube 48 but also the slot 22 of the cannula 6. Even though the angle-cut distal end of the endoscope 14 has moved forward within the inner tube 48 to engage the retractable blade assembly 54, it is still in alignment with the viewing window 58 to observe the tissue being severed at the surgical site.

Also, an advantage of the surgical instrument 2 of the present invention is that it allows the surgeon to extend the cutting blade 24 in any axial position on the cannula 6 such that the transverse carpal ligament may be severed starting from the distal margin thereof or the proximal margin thereof, or any point in between, since the retraction and extension of the cutting blade 24 may be easily controlled by the surgeon during the surgical procedure.

The surgeon may grasp the wing handle 90 of the surgical instrument 2 in one hand while manipulating the switch 82 on the main body assembly 4 of the surgical instrument 2 with the other hand in order to change between the "SCOPE" position, where the cutting blade 24 is retracted within the inner tube 48, and the "BLADE" position, where the cutting blade 24 projects through the slot 56 of the inner tube 48 and the slot 22 of the cannula 6. The blade 24 is extended through the slot 22 of the cannula 6 and the cutting edge 154, 156 of the blade 24 is moved into contact with the transverse carpal ligament. The transverse carpal ligament is severed by either withdrawing the cutting blade 24 or advancing the cutting blade 24 in either axial direction on the cannula 6 which remains detached from the surgical instrument 2 and remains positioned at the surgical site under the transverse carpal ligament.

Alternatively, the cannula 6 may remain fixed to the surgical instrument 2 and, with the blade 24 extended from the slot 22, the cutting edge 156 of the blade 24 is moved into contact with the far margin of the transverse carpal ligament and the transverse carpal ligament is divided by withdrawing the cannula 6 and the surgical instrument 2 towards the entry portal, thereby drawing the cutting edge 156 of the blade 24 through the transverse carpal ligament. The blade 24 may then be retracted back into the cannula 6 when the near margin of the transverse carpal ligament has been reached and severed by switching the surgical instrument 2 to the "SCOPE" position.

After the transverse carpal ligament has been severed, the switch 82 on the surgical instrument 2 may then be rotated by the surgeon to the "SCOPE" position to retract the cutting blade 24 through the cannula slot 22. If, after the cutting operation, and with the cannula 6 detached from the surgical instrument 2 and remaining in place at the surgical site, the endoscope 14, still attached to the surgical instrument 2, may view the surgical site through the transparent cannula 22 and window 58 of the inner tube 48 to visualize the cut edges of the transverse carpal ligament. If any strands of the transverse carpal ligament remain uncut, the blade 24 can then be extended out from the cannula slot 22 again to sever those strands. Alternatively, if the cannula 6 remains attached to the surgical instrument 2 during the cutting procedure and is withdrawn towards the entry portal while the cutting edge 156 of the blade 24, extending through the cannula slot 22, is drawn through the transverse carpal ligament, the cutting blade 24 may then be retracted, and the cannula 6, affixed to the surgical instrument 2, may then be moved back towards the far margin of the transverse carpal ligament through the formed passage, and the optical system of the endoscope 14 is used to visualize the cut edges of the transverse carpal ligament to determine if any strands or sections of the ligament remain uncut.

The surgical instrument 2 of the present invention permits at all times the visualization of the integrity of the underlying median nerve and tendons attached to the digits. While visualizing the nerves and tendons, release is confirmed by passive manipulation of the digits through their range of motion. The cannula 6 is then withdrawn and removed from the entry portal. The cannula 6 is detached from the surgical instrument 2 and properly discarded as medical waste. The wound is closed and a soft bandage is applied. In some cases, a splint is also applied to immobilize the wrist for up to a week.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An endoscopic surgical instrument, which comprises: a main body assembly, the main body assembly having a front end and a rear end disposed axially opposite the front end; a cannula mounted on the front end of the main body assembly, the cannula including a tubular member and a lumen formed in the tubular member and extending axially therein and a slot formed on the tubular member, the slot extending axially on the tubular member and being in communication with the lumen; an inner tube, the inner tube having a proximate end and a distal end situated axially opposite the proximate end, the proximate end of the inner tube being mounted on the front end of the main body assembly and the distal end of the inner tube being receivable by the lumen of the tubular member of the cannula, the inner tube having formed therein a bore extending axially thereon and a blade slot formed thereon, the inner tube being positionable within the lumen of the tubular member of the cannula such that the blade slot is selectively in alignment with the axially-extending slot formed in the tubular member of the cannula; and a retractable cutting blade assembly, the retractable cutting blade assembly being mounted in the bore of the inner tube in proximity to the distal end thereof, the retractable cutting blade assembly having a cutting blade, the cutting blade being positioned to be in alignment with the blade slot formed on the inner tube so as to selectively project outwardly from the inner tube through the blade slot of the inner tube and through the axially-extending slot formed in the tubular member of the cannula and to selectively fully retract into the bore of the inner tube; wherein the main body assembly and the inner tube are configured to receive at least a distal viewing end portion of an endoscope or arthroscope such that a distal end of the endoscope or arthroscope is selectively engagable with the retractable cutting blade assembly; and wherein the main body assembly is configurable to be in at least a first state and a second state, the main body assembly when in the first state preventing the distal end of the endoscope or arthroscope from engaging the retractable cutting blade assembly thereby maintaining the cutting blade in a retracted position within the bore of the inner tube, the main body assembly when in the second state allowing the distal end of the endoscope or arthroscope to engage the retractable blade assembly thereby causing the cutting blade to project outwardly of the inner tube through the blade slot formed therein and outwardly of the tubular member of the cannula through the axially-extending slot formed therein.

2. An endoscopic surgical instrument as defined by claim 1, wherein the cannula is removably attached to the front end of the main body assembly.

3. An endoscopic surgical instrument as defined by claim 2, wherein the cannula includes a cup-shaped member having a diameter which is greater than a diameter of the tubular member of the cannula, the cup-shaped member being attachable to the front end of the main body assembly.

4. An endoscopic surgical instrument as defined by claim 3, wherein the cannula includes a distal end and a proximate end situated axially opposite the distal end;
wherein the main body assembly includes a front end section, the front end section having a front end and a rear end situated axially opposite the front end; and
wherein the cup-shaped member is disposed at the proximate end of the cannula and includes a cylindrical side wall and a conical wall interposed between the cylindrical side wall and the tubular member.

5. An endoscopic surgical instrument as defined by claim 4, wherein the cylindrical side wall of the cup-shaped member of the cannula includes two diametrically opposed slots or recesses positioned thereon, and an opening formed through a thickness of the conical wall.

6. An endoscopic surgical instrument as defined by claim 5, wherein the front end of the front section of the main body assembly includes a projection; and
wherein the opening formed through the thickness of the conical wall of the cup-shaped member of the cannula receives the projection.

7. An endoscopic surgical instrument as defined by claim 5, wherein the front end of the front section of the main body assembly includes a projection; and
wherein the opening formed through the thickness of the conical wall of the cup-shaped member of the cannula receives the projection, the opening formed in the conical wall being in communication and in alignment with the axially-extending slot formed in the tubular member of the cannula so that the cutting blade of the retractable cutting blade assembly which selectively projects from the axially-extending slot formed in the cannula may move on the cannula between at least near the distal end of the cannula and the proximate end of the cannula and through the opening formed in the conical wall of the cup-shaped member, and wherein cooperation between the opening formed in the conical wall of the cup-shaped member of the cannula and the projection formed on the front end of the front section of the main body assembly ensures that the cannula is properly oriented on the main body assembly when it is affixed to the front section thereof.

8. An endoscopic surgical instrument as defined by claim 5, wherein the front end of the front section of the main body assembly includes diametrically opposed protrusions; and
wherein the diametrically opposed slots or recesses formed in the cylindrical side wall of the cup-shaped member of the cannula receive the protrusions formed on the front end of the front section of the main body assembly for removably attaching and securing the cannula to the front section of the main body assembly.

9. An endoscopic surgical instrument as defined by claim 8, wherein the front section of the main body assembly includes two diametrically opposed resilient members, the resilient members being squeezable together radially inwardly of the front section so that the cup-shaped member of the cannula may be fitted thereon, with the protrusions being received by their corresponding slots or recesses formed in the cup-shaped member of the cannula, the resilient members of the front section being biased to expand radially outwardly to secure the cannula in place on the front section of the main body assembly.

10. An endoscopic surgical instrument as defined by claim 9, wherein the front section of the main body assembly has an overall generally cylindrical shape and a central bore passing axially therethrough; and wherein the front section of the main body assembly has formed therein chordally extending slots, the resilient members used to hold the cannula to the main body assembly residing adjacent to respective chordally-extending slots, the chordally-extending slots providing space for the resilient members to flex radially inwardly on the front section.

11. An endoscopic surgical instrument as defined by claim 1, wherein
the tubular member of the cannula includes a flattened top wall, the axially-extending slot being formed through a thickness of the flattened top wall and extending axially thereon over at least a portion of a longitudinal length thereof, the axially-extending slot being provided to allow the retractable cutting blade to project therefrom.

12. An endoscopic surgical instrument as defined by claim 1, wherein at least a portion of the tubular member of the cannula is transparent so that the endoscope or arthroscope whose distal end is received by the surgical instrument and which passes through at least a portion of the lumen of the cannula can view through the transparent portion of the cannula tissue or other anatomical features at a surgical site when a surgeon is performing a procedure on a patent using the surgical instrument.

13. An endoscopic surgical instrument as defined by claim 1, wherein the cannula includes a distal end and a proximate end situated axially opposite the distal end, and wherein the tubular member is formed with a curved end at the distal end of the cannula to define an obturator thereat so that the cannula, when being positioned at a surgical site, will minimize any injury to tissue with which the cannula comes in contact.

14. An endoscopic surgical instrument as defined by claim 13, wherein the retractable cutting blade positioned at the distal end of the inner tube is disposed proximate to but axially inwardly from the obturator end of the cannula.

15. An endoscopic surgical instrument as defined by claim 1, wherein the main body assembly includes a front end section, the front section having a front end and a rear end situated axially opposite the front end, the front section of the main body assembly having formed therein a central bore extending axially therethrough;
wherein at least a portion of the tubular member of the cannula is transparent; and
wherein the inner tube is mounted on the front section of the main body assembly and extends axially outwardly from the front end thereof.

16. An endoscopic surgical instrument as defined by claim 15, wherein the distal end of the inner tube is closed.

17. An endoscopic surgical instrument as defined by claim 15, which further comprises: an alignment ring, the alignment ring being mounted on a side wall of the inner tube and extending radially outwardly therefrom near the proximate end of the inner tube; and wherein the front section of the main body assembly includes two diametrically opposed legs, the legs having radially inwardly facing walls in which are formed arcuate recesses which receive diametrically opposite sides of the alignment ring to secure the proximate end of the inner tube to the front section of the main body assembly.

18. An endoscopic surgical instrument as defined by claim 17, wherein the alignment ring is fixedly positioned on the inner tube at a predetermined location on the axial length thereof so that a distal end portion of the inner tube projects axially from the front end of the front section of the main body assembly a predetermined distance so as to be received by and extend through at least a portion of the axial length of the lumen formed in the tubular member of the cannula; and
wherein a proximate end portion of the inner tube that extends axially beyond the alignment ring passes through at least a portion of the central bore formed axially through the front section of the main body assembly.

19. An endoscopic surgical instrument as defined by claim 15, wherein the inner tube includes a side wall; and
wherein a window is formed in the side wall of the inner tube near the distal end thereof, the window being defined by a cutaway portion of the side wall, the window being provided so that the distal end of an endoscope or arthroscope received by the bore of the inner tube may view through the window formed in the inner tube and through the transparent portion of the tubular member of the cannula tissue or other anatomical structure of a patient at a surgical site during a surgical procedure when the viewing distal end of the endoscope or arthroscope is positioned in proximity to the window formed in the side wall of the inner tube.

20. An endoscopic surgical instrument as defined by claim 19, wherein the window extends circumferentially on the side wall of the inner tube over about a 180 degree portion thereof.

21. An endoscopic surgical instrument as defined by claim 15, wherein the front section of the main body assembly includes an extended, generally tubular portion that projects axially from the rear end thereof, the extended tubular portion having a polygonally-shaped free end through which the central bore of the front section extends.

22. An endoscopic surgical instrument as defined by claim 21, wherein the main body assembly includes a middle section, the middle section being mounted on the extended portion of the front section at the rear end thereof and being at least partially rotatable on the extended portion of the front section, the middle section having a central bore formed axially therethrough, the central bore of the middle section receiving the extended portion of the front section.

23. An endoscopic surgical instrument as defined by claim 22, wherein the extended portion of the front section includes a side wall and has a circumferential groove formed in the side wall thereof, and further includes a retainer ring received in the groove; and
wherein the middle section of the main body assembly includes a front end and a rear end disposed axially opposite the front end, the front end of the middle section being formed with a washer-like disc structure having a central opening, the central opening leading to and communicating with the bore formed through the middle section, the central opening being dimensioned to closely fit onto the extended portion of the front section, the middle section being forced axially onto the extended portion of the front section and over the retainer ring so that the retainer ring holds the middle section in place on the extended portion of the front section but allows the middle section to at least partially rotate thereon.

24. An endoscopic surgical instrument as defined by claim 23, wherein the middle section of the main body assembly has a generally cylindrical shape and includes an outer side wall; and wherein the middle section includes a switch formed as a protruding tab extending radially outwardly from the outer side wall thereof, the switch configured to be movable by finger pressure to facilitate a user of the surgical instrument rotating the middle section on the front section in different positions.

25. An endoscopic surgical instrument as defined by claim 24, wherein the middle section of the main body assembly includes a handle situated near the rear end thereof, the handle being formed as a protruding planar flange extending radially from the cylindrical outer wall of the middle section, the handle being graspable by the user of the surgical instrument during a surgical procedure.

26. An endoscopic surgical instrument as defined by claim 24, wherein the middle section is rotatable on the front section in at least three different positions relative to the front section, the at least three different positions including a first position, a second position and a third position.

27. An endoscopic surgical instrument as defined by claim 26, wherein, when the middle section is in the second position relative to the front section of the main body assembly, the main body assembly is configured to be in a third state to allow the distal end of the endoscope or arthroscope to move axially forward through the bore of the inner tube in a direction towards the distal end of the inner tube so that the distal end of the endoscope or arthroscope may selectively engage the retractable blade assembly to cause the cutting blade to project outwardly through the blade slot formed in the inner tube and the axially-extending slot formed in the cannula.

28. An endoscopic surgical instrument as defined by claim 26, wherein the middle section of the main body assembly may be rotated in opposite circumferential directions on the front section.

29. An endoscopic surgical instrument as defined by claim 28, wherein, when the middle section of the main body assembly is in the second position relative to the front section of the main body assembly, the middle section may be rotated relative to the front section in a first circumferential direction from the second position to the third position, and may be rotated relative to the front section in a second circumferential direction which is opposite to the first circumferential direction from the second position to the first position.

30. An endoscopic surgical instrument as defined by claim 29, wherein the middle section is rotatable in the first circumferential direction relative to the front section of the main body assembly between the second position and the third position by about thirty degrees; and
wherein the middle section is rotatable in the second circumferential direction relative to the front section of the main body assembly between the second position and the first position by about thirty degrees.

31. An endoscopic surgical instrument as defined by claim 26, wherein the front section of the main body assembly includes a cylindrical outer wall, the cylindrical outer wall including first indicia, second indicia and third indicia situated thereon and in proximity to the front end of the middle section rotatably mounted on the first section, the first indicia being spaced circumferentially from the second indicia, and the second indicia being spaced circumferentially from the third indicia.

32. An endoscopic surgical instrument as defined by claim 31, wherein the middle section may be rotated with respect to the front section of the main body assembly such that the switch is in alignment with one of the first indicia when the middle section is in the first position, the second indicia when the middle section is in the second position and the third indicia when the middle section is in the third position.

33. An endoscopic surgical instrument as defined by claim 26, wherein, when the middle section is in the first position relative to the front section of the main body assembly, the main body assembly is configured to be in the first state to prevent the distal end of the endoscope or arthroscope received through the main body assembly and the bore of the inner tube from axially extending more than a predetermined distance in the bore of the inner tube so as not to engage the retractable cutting blade assembly and thereby preventing the retractable cutting blade from projecting outwardly from the blade slot formed in the inner tube and from the axially-extending slot formed in the cannula; and
wherein, when the middle section is in the third position relative to the front section of the main body assembly, the main body assembly is configured to be in the second state to allow the distal end of the endoscope or arthroscope received through the main body assembly and the bore of the inner tube to extend axially through the bore of the inner tube a distance which is equal to or greater than the predetermined distance so as to engage the retractable cutting blade assembly and to cause the cutting blade to project outwardly through the blade slot formed in the inner tube and from the axially-extending slot formed in the cannula.

34. An endoscopic surgical instrument as defined by claim 22, wherein the middle section of the main body section includes a cylindrical inner wall which defines the central bore, the cylindrical inner wall having formed therein near a rear end of the middle section first and second pairs of diametrically opposed arcuate recesses, each recess extending a predetermined circumferential distance on the cylindrical inner wall, the first set of arcuate recesses formed in the cylindrical inner wall being located near the rear end of the middle section, and the second set of arcuate recesses formed in the inner wall of the middle section being spaced axially by a predetermined axial distance from where the first set of arcuate recesses is situated on the inner wall, the predetermined axial distance between the first set of arcuate recesses and the second set of arcuate recesses determining whether the distal end of the endoscope or arthroscope received by the main body assembly and the bore of the inner tube will be permitted to engage or will be prevented from engaging the retractable blade assembly situated at the distal end of the inner tube.

35. An endoscopic surgical instrument as defined by claim 34, wherein the main body assembly further includes a rear section, the rear section being generally cylindrical in shape and including a central bore formed axially therethrough.

36. An endoscopic surgical instrument as defined by claim 35, wherein the front end of the rear section is received by the central bore of the middle section; and
wherein the rear section includes an outer wall, the outer wall having a pair of tabs, each tab protruding from an opposite side of the outer wall of the rear section, the tabs being received in one of the first set of diametrically opposed arcuate recesses formed in the inner wall of the middle section or the more axially forwardly situated second set of diametrically opposed arcuate recesses formed in the inner wall of the middle section.

37. An endoscopic surgical instrument as defined by claim 36, wherein the inner wall of the middle section has formed therein axially extending, diametrically opposed grooves situated in proximity to the rear end thereof, the grooves leading to and communicating with the first set of arcuate recesses and the second set of arcuate recesses, the tabs being receivable by the axially extending, diametrically opposed grooves and movable axially therein when the rear section is axially moved into the bore of the middle section so that the tabs may be moved from the grooves into one of the first set of arcuate recesses and the second set of arcuate recesses when the tabs are axially in alignment with the one of the first set of arcuate recesses and the second set of arcuate recesses and when the middle section of the main body assembly is rotated relative to the front section and the rear section of the main body assembly.

38. An endoscopic surgical instrument as defined by claim 37, wherein the rear section includes a decreased diameter seat formed in the central axial bore thereof;
wherein the rear section further includes an inner wall which defines the central axial bore, a front end portion of the inner wall being formed with substantially the same polygonal shape as the polygonally-shaped extended portion of the front section of the main body assembly so that the polygonal end of the extended portion of the front section is at least partially received by the polygonal front end portion of the bore of the rear section to join the front and rear sections of the main body assembly together but allowing relative axial movement between the front section and the rear section.

39. An endoscopic surgical instrument as defined by claim 38, wherein the main body assembly further includes a compression spring, the compression spring having opposite axial ends, one axial end of the compression spring resting against the decreased diameter seat formed in the bore of the rear section, and the other axial end of the compression spring engaging the polygonally-shaped portion of the extended portion of the front section, the extended portion of the front section being received within the bore of the rear section at the front end portion thereof, wherein the compression spring biases the rear section axially away from the front section.

40. An endoscopic surgical instrument as defined by claim 39, wherein the front end portion of the rear section of the main body assembly includes a cylindrical groove of decreased diameter formed in the outer wall thereof, the groove having an axial length sufficient to allow relative axial movement between the rear section and the front section of the main body assembly so that the tabs of the rear section may transition between and may be received by one of the first set of arcuate recesses formed in the middle section and the second set of arcuate recesses formed in the middle section, the middle section, mounted on the extended portion of the front section, being rotatable at least partially with respect to the front section and the rear section.

41. An endoscopic surgical instrument as defined by claim 40, wherein the middle section of the main body assembly includes a radially extending opening formed through a thickness of the outer wall of the middle section; and wherein the main body assembly further includes a pin, the pin being received by the radially extending opening and extending into the bore of the middle section and is further received within the groove formed in the outer side wall of the rear section of the main body assembly, the pin retaining the rear section to the middle section and to the front section and allowing axial and rotatable partial relative movement between the middle section and the rear section in order to allow the tabs in the rear section to transition between the first set of arcuate recesses and the second set of arcuate recesses formed on the middle section.

42. An endoscopic surgical instrument as defined by claim 35, wherein the rear section of the main body assembly includes a rear end portion having a first diameter and a front end portion having a second diameter, the first diameter of the rear end portion being greater than the second diameter of the front end portion; and
wherein the rear section of the main body assembly further includes a conically-shaped mid-portion interposed between the rear end portion and the front end portion.

43. An endoscopic surgical instrument as defined by claim 42, wherein the rear section of the main body assembly includes a rear wall and an outer wall, the outer wall having a circular groove formed therein, the groove being situated between the rear wall and the conically-shaped mid-portion;
wherein the main body assembly further includes an O-ring, the O-ring being received by the circular groove;
wherein radially-extending openings are formed on diametrically opposite sides of the outer wall of the rear section and situated within the groove; and
wherein the main body assembly further includes ball bearings, each ball bearing being received by a respective radially-extending opening formed in the groove and being situated radially underneath the O-ring.

44. An endoscopic surgical instrument as defined by claim 43, wherein each radially-extending opening extends through a thickness of the outer wall of the rear section of the main body assembly so as to be in communication with the central bore formed axially in the rear section, each opening having a portion thereof formed with a diameter which is less than the diameter of each ball bearing so that only a portion of each ball bearing projects into the central axial bore of the rear section, the ball bearings being held in place in their respective openings and biased radially inwardly towards the central bore of the rear section by the O-ring.

45. An endoscopic surgical instrument as defined by claim 1, wherein the retractable cutting blade assembly positioned at the distal end of the inner tube further includes a top blade housing, a bottom blade housing, an actuator pin, at least one compression spring and a pivot pin; wherein the top blade housing is fixedly mounted in the bore of the inner tube, the top blade housing having a slot formed through a thickness thereof through which the cutting blade may extend from and retract into, the slot in the top blade housing being positioned to be in alignment with the blade slot formed in the inner tube so that the cutting blade may project from and retract into each of the slot in the top blade housing and the blade slot formed in the inner tube; wherein the bottom blade housing is slidable reciprocatingly within the bore of the inner tube, the bottom blade housing being movably joined to the top blade housing by the at least one compression spring, the at least one compression spring biasing the bottom blade housing away from the top blade housing, the bottom blade housing having a surface in which is formed a slot, the slot formed in the bottom blade housing being positioned to be in alignment with the slot formed in the top blade housing, the slot formed in the bottom blade housing at least partially receiving a portion of the cutting blade, the bottom blade housing being engagable by the distal end of the endoscope or arthroscope when the distal end thereof is received by the bore of the inner tube; wherein the pivot pin passes transversely through the bottom blade housing and through the thickness of the cutting blade to allow the cutting blade to pivot thereon and within the slot of the bottom blade housing; wherein the cutting blade has an arcuate slot formed through the thickness thereof, the actuator pin passing transversely through the top blade housing and through the slot formed therein and through the arcuate slot formed through the thickness of the cutting blade, the arcuate slot having a first end and an opposite second end; wherein the actuator pin received by the arcuate slot formed in the cutting blade causes the cutting blade to move within the slot of the top blade housing between an extended position when the actuator pin is located near the first end of the arcuate slot and a retracted position when the actuator pin is located near the second end of the arcuate slot; and wherein, when pressure is exerted on the bottom blade housing by the distal end of the endoscope or arthroscope received by the bore of the inner tube and engaging the retractable cutting blade assembly and to compress the spring thereof, the bottom blade housing moves towards the top blade housing and causes the cutting blade to pivot on the pivot pin on the bottom blade housing, the cutting blade being guided in its movement by the actuator pin situated within the arcuate slot formed therein, the movement of the bottom blade housing towards the top blade housing causing the cutting blade to move from a retracted state, with the actuator pin being situated near the first end of the arcuate slot formed in the cutting blade, to an extended state, with the actuator pin being located near the second end of the arcuate slot formed in the cutting blade such that the cutting blade extends outwardly of the slot formed in the top blade housing and outwardly of the aligned blade slot formed in the inner tube; and wherein, when the distal end of the endoscope or arthroscope is moved in the bore of inner tube in a direction away from the distal end of the inner tube, the compression spring relaxes and causes the bottom blade housing to move away from the top blade housing, resulting in the cutting blade being retracted within the slot formed in the top blade housing and from the slot formed in the inner tube and caused by the blade pivoting on the pivot pin and being affixed to the slidable bottom blade housing, the actuator pin being situated near the second end of the arcuate slot formed in the cutting blade.

46. An endoscopic surgical instrument as defined by claim 1, wherein the cutting blade includes a forward facing sharpened edge and a rearward facing sharpened edge.

* * * * *